US012655104B2

(12) United States Patent
Hergenrother et al.

(10) Patent No.: US 12,655,104 B2
(45) Date of Patent: Jun. 16, 2026

(54) ANTICANCER COMPOUNDS SELECTIVE FOR ER-POSITIVE CANCERS

(71) Applicant: THE BOARD OF TRUSTEES OF THE UNIVERSITY OF ILLINOIS, Urbana, IL (US)

(72) Inventors: Paul J. Hergenrother, Champaign, IL (US); Matthew Boudreau, Newton, MA (US)

(73) Assignee: THE BOARD OF TRUSTEES OF THE UNIVERSITY OF ILLINOIS Urbana, Illinois, Urbana, IL (US)

( * ) Notice: Subject to any disclaimer, the term of this patent is extended or adjusted under 35 U.S.C. 154(b) by 469 days.

(21) Appl. No.: 18/033,173

(22) PCT Filed: Oct. 21, 2021

(86) PCT No.: PCT/US2021/056003
§ 371 (c)(1),
(2) Date: Apr. 21, 2023

(87) PCT Pub. No.: WO2022/087234
PCT Pub. Date: Apr. 28, 2022

(65) Prior Publication Data

US 2023/0391721 A1 Dec. 7, 2023

Related U.S. Application Data

(60) Provisional application No. 63/104,933, filed on Oct. 23, 2020.

(51) Int. Cl.
*C07D 209/34* (2006.01)
*A61P 35/00* (2006.01)
*C07D 401/04* (2006.01)

(52) U.S. Cl.
CPC ............ *C07D 209/34* (2013.01); *A61P 35/00* (2018.01); *C07D 401/04* (2013.01)

(58) Field of Classification Search
CPC ............................ C07D 209/34; C07D 401/04
See application file for complete search history.

(56) References Cited

U.S. PATENT DOCUMENTS

| | | | |
|---|---|---|---|
| 2,855,406 | A | 10/1958 | Otto |
| 3,773,759 | A | 11/1973 | Cusic et al. |
| 2010/0227863 | A1 | 9/2010 | Christensen et al. |

FOREIGN PATENT DOCUMENTS

| | | | |
|---|---|---|---|
| CN | 105102452 | A | 11/2015 |
| CN | 108440378 | A | 8/2018 |
| JP | 2004502654 | | 1/2004 |
| JP | 2010525024 | A | 7/2010 |
| WO | 0198295 | A1 | 12/2001 |
| WO | 2008129075 | A1 | 10/2008 |
| WO | 2020009958 | A1 | 1/2020 |

OTHER PUBLICATIONS

Christensen et al., “Synthesis and Antitumor Effect in Vitro and in Vivo of Substituted 1,3-Dihydroindole-2-ones,” J. Med. Chem., 53, 7140-7145, Jun. 2010.
David et al., “Formal Total Synthesis of Diazonamide A by Indole Oxidative Rearrangement,” Chem. Eur. J., 22, 10867-10876, Jun. 2016.
Di Lorio et al., “Michael Addition of Oxindoles to N-(2-tert-Butylphenyl)maleimides: Efficient Desymmetrization for the Synthesis of Atropisomeric Succinimides with Quaternary and Tertiary Stereocenters,” Synthesis., 49(07):1519-1530, Aug. 2017.
Extended European Search Report of the European Patent Office dated Mar. 12, 2024in EP Application No. 21883881.1; 12pgs.
Goldberg et al., “A Mild Thermal and Acid-Catalyzed Rearrangement of O-Aryl Ethers into ortho-Hydroxy Arenes,” Org. Lett., 7, 20, 4531-4534, Aug. 2005.
Li et al., “Chiral Amine Thiourea-Promoted Enantioselective Michael Addition Reactions of 3-Substituted Benzofuran-2(3H)-ones to Maleimides,” J. Org. Chem., 75, 8697-8700, Nov. 2010.
Liu et al., “Chiral Tertiary Sulfonium Salts as Effective Catalysts for Asymmetric Base-Free Neutral Phase-Transfer Reactions,” Angew. Chem. Int. Ed., 56, 4819-4823, Apr. 2017.
Nicolaou et al., “Chemistry and Biology of Diazonamide A: First Total Synthesis and Confirmation of the True Structure,” J. Am. Chem. Soc., 126, 12888-12896, Mar. 2004.
Andruska et al., “Estrogen Receptor α Inhibitor Activates the Unfolded Protein Response, Blocks Protein Synthesis, and Induces Tumor Regression,” PNAS U S A, 112(15):4737-4742, Apr. 2015.
Boudreau et al., “A Small-Molecule Activator of the Unfolded Protein Response Eradicates Human Breast Tumors in Mice,” Sci Transl Med., 13(603):eabf1383, Jul. 2021.
Christensen et al., “Synthesis and Antitumor Effect in Vitro and in Vivo of Substituted 1,3-Dihydroindole-2-ones,” J. Med. Chem., 53(19):7140-7145, Sep. 2010.
International Search Report and Written Opinion of the ISA/US in PCT/US2021/056003, dated Feb. 22, 2022, 9pgs.
Livezey et al., “Strong and Sustained Activation of the Anticipatory Unfolded Protein Response Induces Necrotic Cell Death,” Cell Death Differ., 25(10):1796-1807, Jun. 2018.

(Continued)

*Primary Examiner* — Paul V Ward
(74) *Attorney, Agent, or Firm* — Haukaas Fortius PLLC; Michael H. Haukaas; Raymond F. Horvath

(57) ABSTRACT

Small molecule ERα biomodulators that kill therapy-resistant ERa positive breast, ovarian, and endometrial cancer cells are disclosed. In one embodiment, the small molecule biomodulator has increased therapeutic utility because of an increased ability to kill therapy-resistant cancer cells compared to BHPI and other conventional therapies (endocrine therapies, tamoxifen, and fulvestrant/ICI). The small molecule biomodulators not only inhibit proliferation of the cancer cells but kills them, which prevents reactivation of tumors years later. Compounds of the invention, such as ErSO-DFP, are effective for treating ERa positive cancers such as breast cancer, ovarian cancer, uterine cancer, cervical carcinoma, endometrial cancer, and the like.

22 Claims, 8 Drawing Sheets

(56) References Cited

OTHER PUBLICATIONS

Natarajan et al., "3,3-Diaryl-1,3-Dihydroindol-2-Ones as Antiproliferatives Mediated by Translation Initiation Inhibition," J Med Chem., 47(8):1882-1885, Apr. 2004.
Peh et al., "Overcoming Resistance to Targeted Anticancer Therapies through Small-Molecule-Mediated MEK Degradation," Cell Chem Biol., 25(8):996-1005., Aug. 2018.
Peh et al., "Overcoming Resistance to Targeted Anticancer Therapies through Small-Molecule-Mediated MEK Degradation," Cell Chem Biol. Author Manuscript, 25(8):996-1005., Aug. 2018.
Puyang et al., "Discovery of Selective Estrogen Receptor Covalent Antagonists for the Treatment of ER' WT and ERa MUT Breast Cancer," Cancer Discov., 8(9):1176-1193, Sep. 2018.
Shapiro et al., "Anticipatory UPR Activation: A Protective Pathway and Target in Cancer," Trends Endocrinol Metab. Author Manuscript, 27(10):731-741, Oct. 2016.
Shapiro et al., "Anticipatory UPR Activation: A Protective Pathway and Target in Cancer," Trends Endocrinol Metab., 27(10):731-741, Oct. 2016.
Zheng et al., "Targeting Multidrug-Resistant Ovarian Cancer Through Estrogen Receptor a Dependent ATP Depletion Caused by Hyperactivation of the Unfolded Protein Response," Oncotarget,9(19):14741-14753, Jul. 2016.

A.

B.

A.

B.

A.

B.

A.

B.

ANTICANCER COMPOUNDS SELECTIVE FOR ER-POSITIVE CANCERS

RELATED APPLICATIONS

This application is a National Stage filing under 35 U.S.C. § 371 of International Application No. PCT/US2021/056003, filed Oct. 21, 2021, which claims the benefit of U.S. Provisional Patent Application No. 63/104,933, filed Oct. 23, 2020, which applications are incorporated herein by reference.

BACKGROUND OF THE INVENTION

Targeting ERα directly or indirectly has been the flagship targeted strategy for treating ERα+ breast cancers. Such strategies are termed as endocrine therapies, as they seek to block the canonical functions of ERα in induction of cell growth and proliferation. Although patients initially benefit from endocrine therapy (typically with tamoxifen, fulvestrant, anastrozole, and others), drug-resistance and tumor regrowth is inevitable and represents a major clinical challenge. Even with the recent combining of endocrine therapy with CDK4/6 or PI3KCA inhibitors, drug-resistant, lethal disease is still pervasive. These resistant tumors typically maintain their ERα overexpression, suggesting that drugs leveraging ERα, especially those acting through new mechanisms, may provide a meaningful clinical benefit to a diverse patient population that is typically considered drug resistant and is not well-served by other therapeutic options.

The traditional unfolded protein response (UPR) is characterized by signaling in response to insufficient protein-folding capacity. There is another form of the UPR, the anticipatory UPR (a-UPR), which is activated by cells in 'anticipation' of future hyperactivated growth. This a-UPR is a conserved mechanism across hormone-specific receptors including ERα, androgen receptor, epidermal growth factor receptor, and others; induction of the a-UPR can be considered as a non-canonical function of ERα. While the a-UPR is cytoprotective and has been correlated with drug-resistance in a variety of settings, sustained activation is toxic to cancer cells and represents an opportunity to convert a tumor protective pathway into a potent and selective anticancer strategy.

We recently reported the small molecule ErSO, a compound that hyperactivates the ERα-dependent a-UPR in ERα+ cancer cells leading to eradication of ERα+ breast tumors in multiple mouse models. ErSO maintains activity against breast cancer cell lines that contain mutations in ERα (Y537S and D538G) representing major clinical resistance mechanisms to endocrine therapy. The selectivity of ErSO for ERα+ cells in culture at short incubation times (e.g. 6 or 24 hours) is impressive, with >350 fold difference in cellular $IC_{50}$ between ERα+ and ERα− cancer cell lines. In addition, knock-in of ERα into ERα-negative MDA-MB-231 triple-negative breast cancer cells dramatically sensitizes these cells to ErSO both in cell culture and in xenograft models. The ability of ErSO to leverage this non-canonical activity of ERα (induction of the a-UPR) likely enables ErSO to induce tumor regressions, contrasting the cytostatic activity typically observed with endocrine therapy.

Accordingly, new small molecule therapeutic agents that are cytotoxic, and not merely cytostatic, are urgently needed to provide more efficacious cancer therapy.

SUMMARY

Estrogen receptor alpha-positive (ERα+) breast cancers are the most common type of this disease, with >200,000 new cases diagnosed annually in the United States. For these cancers, ERα drives tumor growth and disease progression, and thus targeting ERα directly with ERα antagonists and degraders (e.g., tamoxifen, fulvestrant) or indirectly with aromatase inhibitors has been a successful therapeutic strategy, with significant gains in overall survival for these patients. However, such treatments are rarely curative, and patients typically succumb to metastatic, drug-resistant (through ERα mutation and other mechanisms) disease. The small molecule, ErSO, which induces potent ERα-dependent death of ERα+ breast cancer cells through a mechanism distinct from clinically approved drugs that target ERα, namely hyperactivation of the anticipatory unfolded protein response. ErSO has remarkable activity in multiple mouse models of ERα+ breast cancer, in many cases inducing complete tumor eradication. Importantly, ErSO is potent and effective even when evaluated in breast cancer cell lines and preclinical tumor models that are resistant to endocrine therapy via mutated ERα. While ErSO has tremendous promise as a new drug to target ERα+ tumors, at high concentrations and long incubation times it does have some effects on ERα-negative (ERα−) cells in culture.

Herein we report the construction of modified versions of ErSO, with a major focus on establishing a structure-activity relationship and identifying new variants with an even wider differential activity between ERα+ and ERα− cells. In the course of these studies, we discovered ErSO-DFP, a compound that maintains outstanding efficacy for inducing death of ERα+ breast cancer cells in cell culture, has markedly enhanced selectivity for ERα+ cancer cells over ERα− cancer cells, increased in vivo tolerability, and a striking antitumor effect in vivo, inducing dramatic regression of large ERα+ tumors in a murine orthotopic xenograft model. ErSO-DFP and related molecules represent an intriguing new class of compounds for the treatment of ERα+ cancers.

In one embodiment, the invention therefore provides a compound of Formula I:

(I)

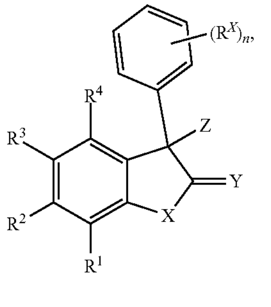

wherein

X is O, S, or $NR^A$;

Y is O, S, or $NR^A$;

each $R^A$ is independently H, alkyl, or a nitrogen protecting group;

$R^1$ is trifluoromethyl, trifluoromethoxy, alkyl, cycloalkyl, heterocycle, aryl, heteroaryl, halo, $—OR^B$, $—SR^B$, or $—N(R^B)_2$;

$R^2$, $R^3$ and $R^4$ are each independently H, trifluoromethyl, alkyl, cycloalkyl, heterocycle, aryl, heteroaryl, halo, $—OR^B$, $—SR^B$, or $—N(R^B)_2$;

each $R^B$ is independently H, trifluoromethyl, alkyl, or a heteroatom protecting group;

each $R^X$ is independently OH, halo, alkyl, $—OR^C$, $—SR^C$, $—S(═O)_2R^C$;

each $R^C$ is independently H, trifluoromethyl, alkyl, or a heteroatom protecting group;

n is 0, 1, 2, 3, 4, or 5; and

Z is a 3-8 membered nitrogen-containing heterocycle optionally substituted with one or more substituents;

wherein each alkyl, cycloalkyl, heterocycle, aryl, and heteroaryl is optionally substituted with one or more substituents;

or a salt thereof.

When substituted, the alkyl, cycloalkyl, heterocycle, aryl, and heteroaryl can be substituted one or more substituents selected from OH, halo, nitro, alkyl, and group of substituents as defined for substituted groups discussed herein below. For example, an alkyl can be substituted with two or three halo groups to provide dihalo-alkyl or a trihalo-alkyl (such as trifluoromethyl), respectively. Accordingly, any alkyl group or substituent of Formula I can be substituted to result in a trifluoromethyl group.

In one embodiment, X is NH and Y is O. In some embodiments, $R^1$ is $CF_3$ or Me. In various embodiments, $R^2$, $R^3$ and $R^4$ are each independently H or halo. In a specific embodiment, $R^X$ is OH. In various embodiments, n is 1, 2, or 3.

In certain embodiments, $R^X$ is OH and n is 1, 2, or 3. Various embodiments include compounds of Formula I wherein $R^X$ is OH, n is 1 or 2, and the $R^X$ groups are located at the meta or para positions of the phenyl ring to which they are attached, or wherein $R^X$ is OH, n is 1, and the $R^X$ group is located at the para position of the phenyl ring to which it is attached.

In some embodiments, Z is a 3-. 4-, 5-, 6-, 7-, or 8-membered nitrogen-containing heterocycle attached to Formula I by the nitrogen atom of the heterocycle. In various embodiments, the heterocycle can be substituted by one or two halo groups. In additional embodiments, the heterocycle is piperidine substituted by one or two fluoro groups at the 3-position of the piperidine ring. In further embodiments, the heterocycle is piperidine, morpholine, piperazine, pyrrolidine, azepane, aziridine, azetidine, or azocane each optionally substituted with one to six substituents. In some embodiments, Z is 4,4-difluoropiperidinyl, 3,3-difluoropyrrolidinyl, or 3,3,4,4-tetrafluoropyrrolidinyl.

In one embodiment, the compound of Formula I is levorotatory. In alternate embodiments, the compound is of Formula I dextrorotatory.

In some embodiments, a compound of Formula I is a compound of Formula II or III:

(II)

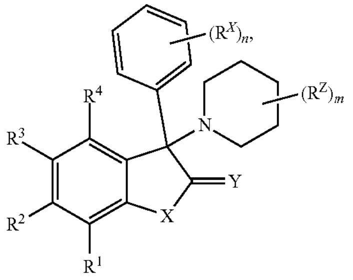

or

-continued (III)

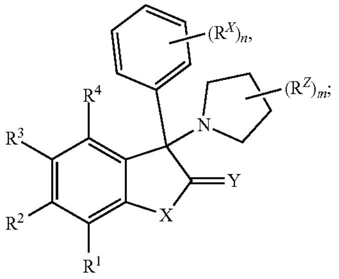

wherein each $R^Z$ is independently OH, halo, nitro, alkyl, $—OR^D$, $—SR^D$, $—S(=O)_2R^D$; wherein each $R^D$ is independently H, trifluoromethyl, alkyl, or a heteroatom protecting group; and m is 0-12; or a salt thereof.

In some embodiments, X is NH; Y is O; $R^1$ is $CF_3$ or Me; $R^2$, $R^3$ and $R^4$ are each independently H or halo; $R^X$ is OH, and n is 1, 2, or 3. In various embodiments, m is 2 and each $R^Z$ is halo. In additional embodiments, each halo is fluoro.

In some specific embodiments, the compound of Formula I, II, or III is 2, 24, or 26:

(2)

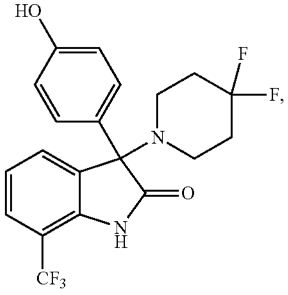

(24)

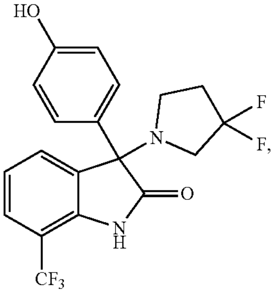

or (26)

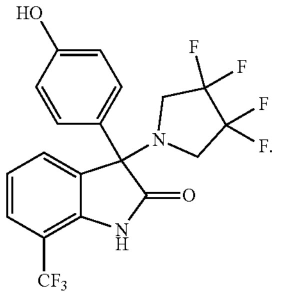

In another specific embodiment, the compound of Formula I or II is ErSO-DFP:

(ErSO-DFP)

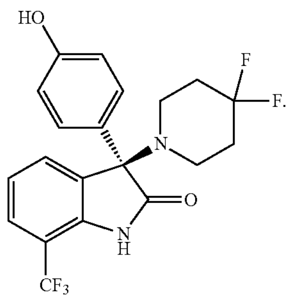

The invention also provides a pharmaceutical composition comprising the compound of Formula I or II in combination with a pharmaceutically acceptable carrier.

The invention further provides a method of treating an ERα positive cancer comprising administering to subject having an ERα positive cancer a therapeutically effective amount of a compound of Formula I or II, thereby treating the ERα positive cancer. In some embodiments, the ERα positive cancer is breast cancer, ovarian cancer, uterine cancer, cervical carcinoma, or endometrial cancer. In a specific embodiment, the compound is ErSO-DFP.

Compounds of the formulas described herein can bind to the alpha estrogen receptor (ERα) and kill or inhibit the growth of cancer cells by hyperactivation of the unfolded protein response (UPR) in the endoplasmic reticulum. In various embodiments, the compound of Formula I is cytotoxic. Accordingly, in various embodiments, cancer can be, for example, breast cancer, ovarian cancer, uterine cancer, cervical carcinoma, endometrial cancer, lung cancer, pancreatic cancer, prostate cancer, or colon cancer.

The invention thus provides novel compounds of Formulas I-III, intermediates for the synthesis of compounds of Formulas I-III, as well as methods of preparing compounds of Formulas I-III. The invention also provides compounds of Formulas I-III that are useful as intermediates for the synthesis of other useful compounds. The invention provides for the use of compounds of Formulas I-III for treating of cancer in a mammal, such as a human. The compound administered can be in the form of a composition that includes a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
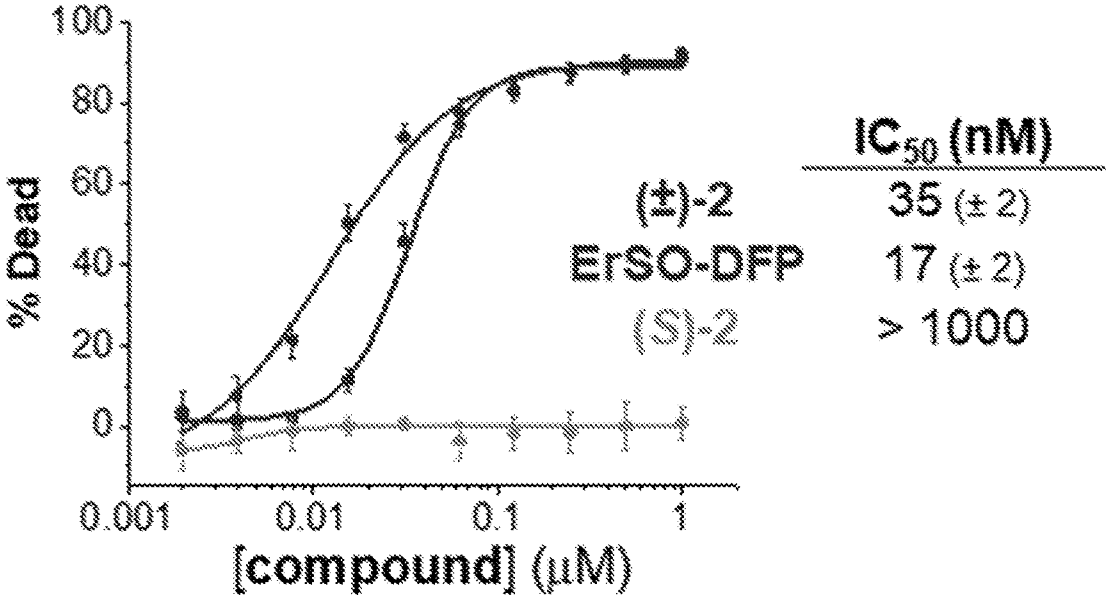
FIG. 1. ErSO-DFP is the active anticancer agent with superior LipE relative to its progenitor, ErSO. A, Biological activity of racemic 2 ((±)-2), ErSO-DFP, and (S)-2 against MCF-7 cells incubated with compound for 24 hours. Cell viability was assessed by alamar blue fluorescence. Raptinal (100 μM) was used as the 100% dead control. Data is shown as mean±s.e.m.; n≥2 independent replicates. B, Lipophilic efficiencies of ErSO and ErSO-DFP. Increases in LipE are often associated with more 'drug-like' character.
Figure 1:
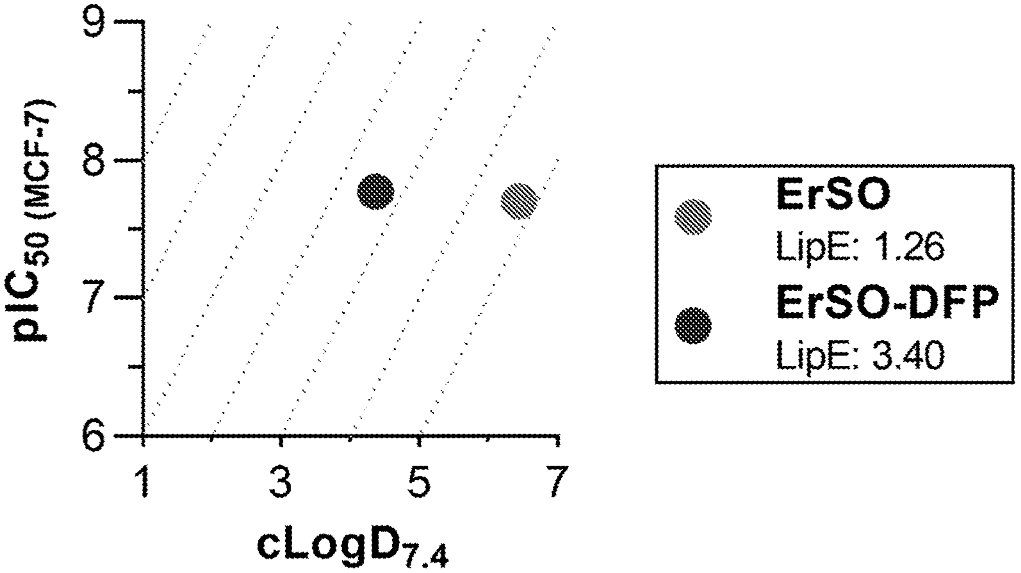

Based on data from pre-clinical models, ErSO appears to have a wide therapeutic window; it is tolerated at oral doses greater than 150 mg/kg in mice and canines. However, there are traits of ErSO that, if altered, might lead to an even more promising drug. First, as compared to oral dosing, the maximum tolerated dose of ErSO in mice is significantly lower when administered intravenously (20 mg/kg), and there appears to be some species-specific sensitivity, with lower maximal tolerated doses in rats. Second, as shown and as detailed further herein, at longer incubation times and higher concentrations the selectivity of ErSO for induction of cell death in ERα+ versus ERα− cancer cells begins to erode in some cases. Herein we sought to construct and evaluate novel compounds related to ErSO, with the goal of identifying new leads with minimized ERα-independent effects; we hypothesized that such an optimized compound would have a wider therapeutic window in vivo. In addition to their translational promise, more selective compounds would also be superior probes for robust and clean ERα-dependent activation of the a-UPR. Here we report ErSO-DFP ((R)-2, Chart 1), a compound with markedly increased selectivity for ERα+ cancer cells in culture, ErSO-like a-UPR activation and potency, a larger therapeutic window in vivo, and superior drug-like properties, all while maintaining the ability to induce profound tumor regression in a mouse model of ERα+ breast cancer at low doses.

Chart 1. Chemical Structures of ErSO and ErSO-DFP.

ErSO 1

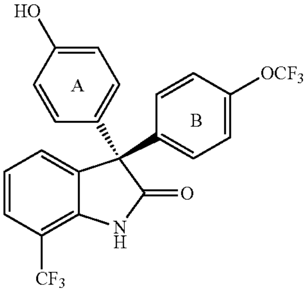

ErSO-DFP (R)-2

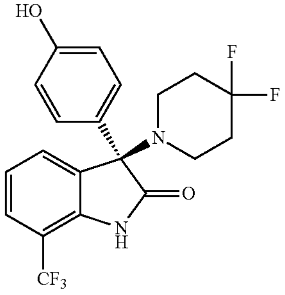

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five substituents on the ring.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compounds and compositions described herein may be administered with additional compositions to prolong stability and activity of the compositions, or in combination with other therapeutic drugs.

The terms “inhibit”, “inhibiting”, and “inhibition” refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term “substantially” as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term “comprising” is used herein, options are contemplated wherein the terms “consisting of” or “consisting essentially of” are used instead. As used herein, “comprising” is synonymous with “including,” “containing,” or “characterized by,” and is inclusive or open-ended and does not exclude additional, unrecited elements or method steps. As used herein, “consisting of” excludes any element, step, or ingredient not specified in the aspect element. As used herein, “consisting essentially of” does not exclude materials or steps that do not materially affect the basic and novel characteristics of the aspect. In each instance herein any of the terms “comprising”, “consisting essentially of” and “consisting of” may be replaced with either of the other two terms. The disclosure illustratively described herein may be suitably practiced in the absence of any element or elements, limitation, or limitations not specifically disclosed herein.

The term “halo” or “halide” refers to fluoro, chloro, bromo, or iodo. Similarly, the term “halogen” refers to fluorine, chlorine, bromine, and iodine.

The term “alkyl” refers to a branched or unbranched hydrocarbon having, for example, from 1-20 carbon atoms, and often 1-12, 1-10, 1-8, 1-6, or 1-4 carbon atoms. As used herein, the term “alkyl” also encompasses a “cycloalkyl”, defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at carbon or two different carbon atoms of a carbon chain. Similarly, alkenylene and alkynylene are respectively an alkene and an alkyne having two free valences at two different carbon atoms.

The term “cycloalkyl” refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term “heterocycloalkyl” or “heterocycle” refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably 3 to 10 membered, more preferably 4 to 7 membered. Examples of suitable heterocycloalkyl groups include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, 1,4-oxathiapane, and the like. The heterocycle can be substituted with one or more substituents.

The term “aromatic” refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term “aryl” refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term “heteroaryl” refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of “substituted”. Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups (substituents) include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', $OC(O)N(R')_2$, CN, $CF_3$, $OCF_3$, R', O, S, C(O), S(O), methylenedioxy, ethylenedioxy, $N(R')_2$, SR', SOR', $SO_2R'$, $SO_2N(R')_2$, $SO_3R'$, C(O)R', C(O)C(O)R', $C(O)CH_2C(O)R'$, C(S)R', C(O)OR', OC(O)R', $C(O)N(R')_2$, $OC(O)N(R')_2$, $C(S)N(R')_2$, $(CH_2)_{0-2}NHC(O)R'$, N(R')N(R')C(O)R', N(R')N(R')C(O)OR', $N(R')N(R')CON(R')_2$, $N(R')SO_2R'$, $N(R')SO_2N(R')_2$, N(R')C(O)OR', N(R')C(O)R', N(R')C(S)R', $N(R')C(O)N(R')_2$, $N(R')C(S)N(R')_2$, N(COR')COR', N(OR')R', $C(=NH)N(R')_2$, C(O)N(OR')R', or C(=NOR')R' wherein R' can be hydrogen or a carbon-based moiety (e.g., ($C_1$-$C_6$)alkyl), and wherein the carbon-based moiety can itself be further substituted. When a substituent is monovalent, such as, for example, F or Cl, it is bonded to the atom it is substituting by a single bond. When a substituent is divalent, such as O, it is bonded to the atom it is substituting by a double bond; for example, a carbon atom substituted with O forms a carbonyl group, C=O.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity, or one enantiomer is present in very low quantities, for example, 0.01%, 0.001% or 0.0001%.

The term "$IC_{50}$" is generally defined as the concentration required to kill 50% of the cells in 24 hours.

The name "ErSO-DFP" refers to the compound (R)-3-(4,4-difluoropiperidin-1-yl)-3-(4-hydroxyphenyl)-7-(trifluoromethyl)indolin-2-one.

Embodiments of the Invention

In each formula described herein, when a variable element of Formula I or Formula II is optionally substituted, it can be substituted with one or more substituents, such as one or more of the substituents described in the definition of substituents herein. Alkyl optionally substituted with one or more substituents can be, for example, alkyl substituted with one to six substituents, one to five substituents, one to four substituents, one to three substituents, one or two substituents, or one substituent. Alkyl optionally substituted with one or more substituents includes, for example, halo-substituted alkyl groups such as $CF_3$, $CHF_2$, $CH_2F$, $CH_2CF_3$, $CF_2CH_3$, or $CF_2CF_3$.

In some embodiments, the compound of Formula I is the (S)-enantiomer. In other embodiments, the compound of Formula I is the (R)-enantiomer. Likewise, in some embodiments, the compound of Formula II is the (S)-enantiomer and in other embodiments, the compound of Formula II is the (R)-enantiomer. If substituents on Formula I or Formula II result in a compound having more than one stereocenter, the (R) and (S) designations described in this paragraph refer to the location of the stereocenter of the compound corresponding to the stereocenter found in ErSO-DFP.

In some embodiments, the compound is (R)-3-(4,4-difluoropiperidin-1-yl)-3-(4-hydroxyphenyl)-7-(trifluoromethyl)indolin-2-one. In some embodiments, the compound is (S)-3-(4,4-difluoropiperidin-1-yl)-3-(4-hydroxyphenyl)-7-(trifluoromethyl)indolin-2-one. In some embodiments, the compound is 3-(4-hydroxyphenyl)-3-(piperidin-1-yl)-7-(trifluoromethyl)indolin-2-one; 3-(4,4-difluoro-3-methylpiperidin-1-yl)-3-(4-hydroxyphenyl)-7-(trifluoromethyl)indolin-2-one; 3-(4-hydroxyphenyl)-3-morpholino-7-(trifluoromethyl)indolin-2-one; 3-(azepan-1-yl)-3-(4-hydroxyphenyl)-7-(trifluoromethyl)indolin-2-one; 3-(4-hydroxyphenyl)-3-(piperazin-1-yl)-7-(trifluoromethyl)indolin-2-one; 3-(4-hydroxyphenyl)-3-(4-hydroxypiperidin-1-yl)-7-(trifluoromethyl)indolin-2-one; 3-(4-hydroxyphenyl)-3-(4-(trifluoromethoxy)piperidin-1-yl)-7-(trifluoromethyl)indolin-2-one; 3-(4-fluoropiperidin-1-yl)-3-(4-hydroxyphenyl)-7-(trifluoromethyl)indolin-2-one; 3-(3,3-difluoropiperidin-1-yl)-3-(4-hydroxyphenyl)-7-(trifluoromethyl)indolin-2-one; 3-(3,3-difluoropyrrolidin-1-yl)-3-(4-hydroxyphenyl)-7-(trifluoromethyl)indolin-2-one; 3-(3,3-difluoroazetidin-1-yl)-3-(4-hydroxyphenyl)-7-(trifluoromethyl)indolin-2-one; or 3-(4-hydroxyphenyl)-3-(3,3,4,4-tetrafluoropyrrolidin-1-yl)-7-(trifluoromethyl)indolin-2-one.

In other embodiments, the compound is (R)-3-(3,3-difluoropyrrolidin-1-yl)-3-(4-hydroxyphenyl)-7-(trifluoromethyl)indolin-2-one or (R)-3-(4-hydroxyphenyl)-3-(3,3,4,4-tetrafluoropyrrolidin-1-yl)-7-(trifluoromethyl)indolin-2-one.

The compound of Formula I and Formula II can kill or inhibit the growth of cancer cells by hyperactivation of the unfolded protein response (UPR) in the endoplasmic reticulum. The cancer cells or resulting tumor can be ERα positive. In certain embodiments, the compounds are cytotoxic. In various embodiments, the cancer cells are breast cancer cells, ovarian cancer cells, endometrial cancer cells, or other EP positive cancers known in the art.

The compound can be administered orally, by injection, subcutaneously, sublingually, rectally, by infusion, intravenously, or by other methods known to those of skill in the art.

Results

Assessment of ErSO as a lead reveals lipophilicity as a major optimizable parameter. ErSO is considered quite lipophilic with a $clogD_{7.4}$ of 6.44. While lipophilicity can lead to entropic and enthalpic gains for target binding, molecules that are too hydrophobic often have poor "drug-like" properties (e.g. high clearance, inhibition of off-targets, poor oral bioavailability and the propensity to inhibit key safety ion channels like hERG). Lipophilicity was envisioned as a parameter ripe for modulation through systematic changes to Ring A/B of ErSO (Chart 1). Therefore $cLogD_{7.4}$, cellular potency and selectivity (that is, differential effects on ERα+ and ERα− cancer cells), and the lipophilic efficiencies (LipE) were prioritized for the identification of promising derivatives. Specifically, we hypothesized that compounds with lower $clogD_{7.4}$ and higher LipE would be superior compounds as assessed by in vivo evaluation of tolerability and efficacy, in line with multiple drug development campaigns.

Exploration of the Phenolic Pharmacophore (Ring A Perturbations)

There are multiple reports on 3-(4-hydroxyphenyl)indoline-2-ones as an anticancer pharmacophore. A consistent observation is the necessity of is at least one phenol for anticancer activity. While derivatives with substituents on the phenol ring are unlikely to provide major changes in lipophilicity, altering the phenol's electronics can provide clues as to the optimal pKa for anticancer activity, and phenols with major changes in pKa may have altered metabolism (e.g. glucuronidation rates) in vivo. To explore the structure-activity relationships (SAR) of ErSO's phenol, multiple derivatives with modifications to the phenol ring were evaluated. A facile and modular synthetic route was utilized to construct these derivatives through addition of the lithiated B-ring to 7-trifluoroisatin (3) forming tertiary alcohol 4, with alterations then introduced through Friedel-Crafts-type reactions, providing compounds 5-13 (Scheme 1).

Scheme 1. Modular Synthesis of Phenol Derivatives.

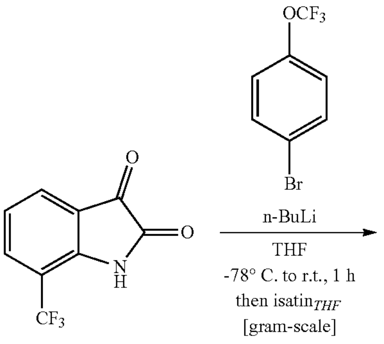

3

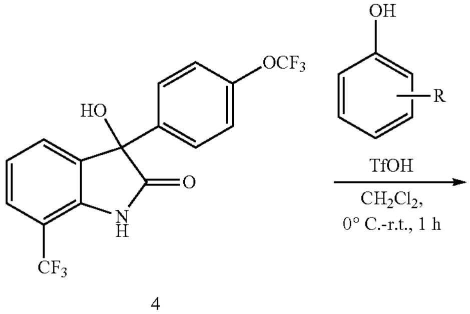

4
65%

-continued

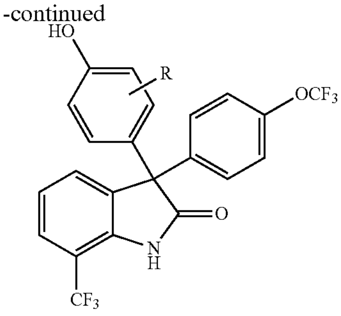

5-13
39-91% n-BuLi: n-butyllithium, TfOH: triflic acid, isatin$_{THF}$: 7-trifluoromethylisatin (3) dissolved in THF, THF: tetrahydrofuran.

The derivatives synthesized through this process, the predicted pKa of the phenolic OH, and anticancer activity against MCF-7 cancer cells (an ERα+ breast cancer cell line) are displayed in Table 1. Of note when analyzing biological data herein, we and other (Sci. Transl. Med., 2021, 13, 603) have found that for this class of compounds only one enantiomer (often the (R)-enantiomer) has anticancer activity; thus, it is assumed that racemic compounds have one half the potency of their enantiopure counterparts. Interestingly, fluorine substitution at various positions (e.g., compounds 5-8) on the ring provides compounds with predicted phenol pKa values ranging from 7.50-8.39; in general, such substitutions are relatively tolerated with the ortho-fluorinated derivative (5) being the most active. There is loss of activity with compound 6, where the phenol is predominately deprotonated at physiological pH. The immutability of the phenol is strongly indicated by the lack of activity observed for trifluoromethyl anisole 9. Compounds with ortho-hydroxylation of the phenol can maintain potency, demonstrated by compound 10 and its single enantiomer (ErSO—OH, (S)-10); ErSO—OH is a minor metabolite found during in vitro metabolite assessment of ErSO (albeit only found at <1% abundance). In contrast, compounds 11-13, with o-alkylations on the phenol ring are inactive. In summary, even minor changes in the phenol ring can lead to profound losses in activity.

Given the focus on significantly altering ErSO's lipophilicity, changes centered around the phenol were thus unproductive, with the only exception of the catechol ErSO—OH, which has a decreased cLogD$_{7.4}$ (6.13) and maintained potency. Initial in vivo tolerability assessments of ErSO—OH, demonstrated a proof-of-concept that decreased clogD$_{7.4}$ could lead to greater intravenous tolerability in mice, however no gains in rat tolerability were observed for this compound. Of note, there are well-reported challenges in developing catechols as drugs, with propensity for oxidation, orthoquinone formation, and subsequent promiscuous reactivity.

TABLE 1

Summary of Ring A Derivatives' Parameters and Cellular Potencies.

| Compound | 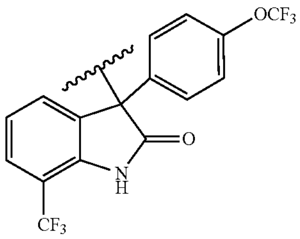 [SMILES: *C1(c2ccc(OC(F)(F)F)cc2)C(=O)Nc2c(C(F)(F)F)cccc21] | Phenolic pKa[a,b] | cLogD$_{7.4}$[a] | $IC_{50}$ (nM)[c] |
|---|---|---|---|---|
| ErSO (1) | 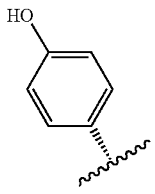 | 9.48 | 6.44 | $20_{(\pm 2)}$ |
| 5 | 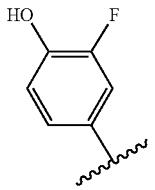 [SMILES: *c1ccc(O)c(F)c1] | 8.39 | 6.54 | $33_{(\pm 1)}$ |
| 6 | 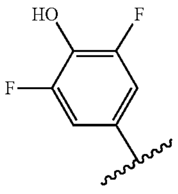 [SMILES: *c1cc(F)c(O)c(F)c1] | 7.50 | 6.48 | >1000 |

TABLE 1-continued
Summary of Ring A Derivatives' Parameters and Cellular Potencies.
| Compound | 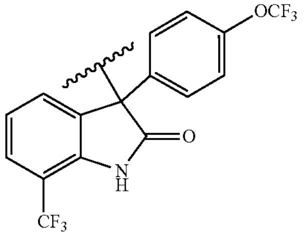 | Phenolic pKa[a,b] | $cLogD_{7.4}$[a] | $IC_{50}$ (nM)[c] |
|---|---|---|---|---|
| 7 | 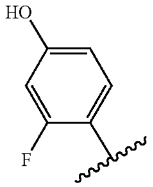 [SMILES: *c1ccc(O)cc1F] | 8.51 | 6.55 | $177_{(\pm 25)}$ |
| 8 | 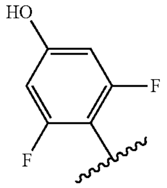 [SMILES: *c1c(F)cc(O)cc1F] | 7.56 | 6.50 | $549_{(\pm 18)}$ |
| 9 | 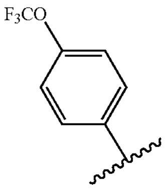 [SMILES: *c1ccc(OC(F)(F)F)cc1] | — | 18.18 | >1000 |
| 10 | 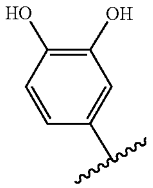 [SMILES: *c1ccc(O)c(O)c1] | 9.23, 12.44 | 6.13 | $49_{(\pm 9)}$ |
| ErSO-OH ((S)-10) | 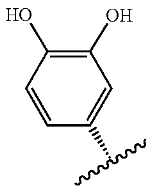 | 9.23, 12.44 | 6.13 | $24_{(\pm 4)}$ |
| 11 | 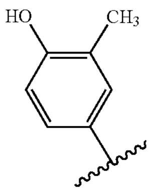 [SMILES: *c1ccc(O)c(C)c1] | 9.84 | 6.96 | >1000 |

TABLE 1-continued

Summary of Ring A Derivatives' Parameters and Cellular Potencies.

| Compound | 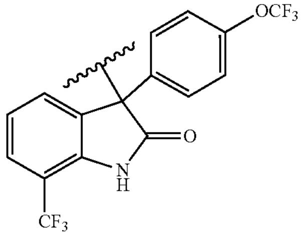 | Phenolic pKa[a,b] | $cLogD_{7.4}$[a] | $IC_{50}$ (nM)[c] |
|---|---|---|---|---|
| 12 | 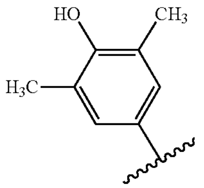 | 10.19 | 7.47 | >1000 |
| 13 | 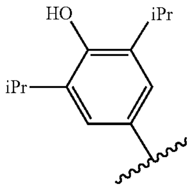 [SMILES: *c1cc(C(C)C)c(O)c(C(C)C)c1] | 10.44 | 8.93 | >1000 |

[a]pKa and $cLogD_{7.4}$ was calculated using ChemAxon MarvinSketch.
[b]pKa is reported for Ring A acidic protons.
[c]To determine $IC_{50}$, MCF-7 cells were incubated with compound for 24 hours and viability measured via Alamar blue fluorescence.
Raptinal (100 μM) was used as the 100% dead control.
Data is shown as mean ± s.e.m .;
n ≥ 2 independent replicates. iPr: isopropyl.

Exploration of Ring B, Discovery of Amine-Containing Species

While other 3-(4-hydroxyphenyl)indoline-2-ones have altered B-rings and maintain potent anticancer activity in cell culture and in vivo, there has been little exploration beyond simple unsubstituted cycloalkanes (i.e. cyclopentyl, cyclohexyl, cycloheptyl). The dearth of diversity at this position is likely a consequence of the difficulty in synthesizing substituted compounds of this type in a diastereoselective and modular fashion. We envisioned that alteration of this ring with polar functionality could lead to biologically active derivatives with tunable changes in lipophilicity. Efforts focused on incorporation of nitrogen-containing heterocycles, which would afford decreases in overall lipophilicity; such compounds are unprecedented on the 3-(4-hydroxyphenyl)indoline-2-one scaffold.

The synthesis of these nitrogen-containing compounds (Scheme 2) proceeds in a similar manner to the route used to access Ring A derivatives, starting with nucleophilic attack of 7-trifluoroisatin (3) with an aryl organolithium generated in situ to form tertiary alcohol 14. As the Friedel-Crafts route in Scheme 1 is precluded for these new target compounds, to incorporate amine nucleophiles, generation of unstable tertiary chloride 15 was followed by reaction with the appropriate nitrogen-containing heterocycle, and TBS deprotection (Scheme 2) provided final compounds 2 and 16-21 (Table 2).

Scheme 2. Modular Synthesis of B-Ring Derivatives.

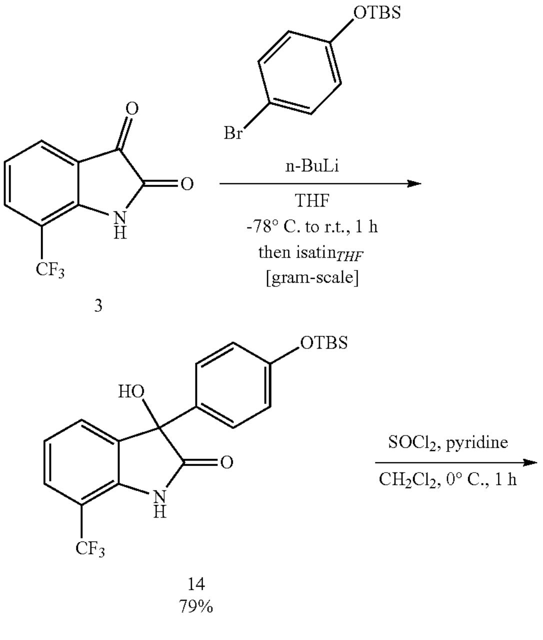

-continued

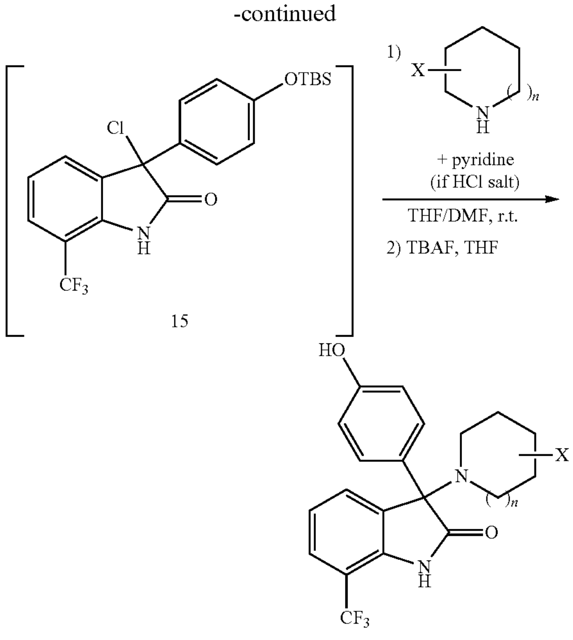

15

2, 16-21
41-83% n-BuLi: n-butyllithium, TBS: tert-butyldimethylsilyl, $SOCl_2$: thionyl chloride, TBAF: tetrabutylammonium fluoride, THF: tetrahydrofuran, DMF: dimethylformamide.

The activity of these novel nitrogen-containing compounds is summarized in Table 2. Notably, the $cLogDz_4$ values (ranging from 2.61-4.85) are markedly lower than their bis-aryl counterparts. Assessment against MCF-7 cells in culture revealed that, strikingly, 4,4-difluorosubstituted piperidines 2 and 17 maintained potent anticancer activity, in stark contrast with compound 16, which lacks 4,4-difluorination. Compound 17 is a mixture of diastereomers and their corresponding enantiomers (4 total compounds) and suggests the possibility that compounds with branching from the 3-position of the 4,4-difluoropiperdine can maintain potency. Interestingly, it does appear that only one species is active as evidenced by its doubled $IC_{50}$ as compared to 2. All other compounds tested in this set (18-21) lack potent activity.

TABLE 2

Summary of Ring B Derivatives' Parameters and Cellular Potencies.

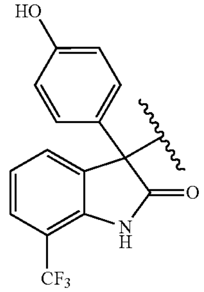 [SMILES: *C1(c2ccc(O)cc2)C(=O)Nc2c(C(F)(F)F)cccc21]

| Compound | | $cLogD_{7.4}$[a] | $IC_{50}$ (nM)[b] |
|---|---|---|---|
| 2 | 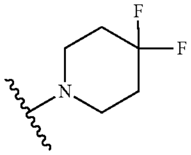 [SMILES: *N1CCC(F)(F)CC1] | 4.37 | $35_{(\pm 3)}$ |

TABLE 2-continued

Summary of Ring B Derivatives' Parameters and Cellular Potencies.

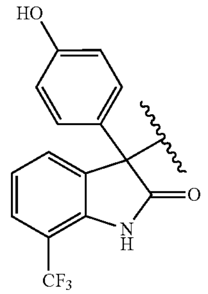

| Compound | | $cLogD_{7.4}$[a] | $IC_{50}$ (nM)[b] |
|---|---|---|---|
| 16 | 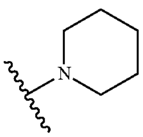 [SMILES: *N1CCCCC1] | 4.14 | >1000 |
| 17[c] | 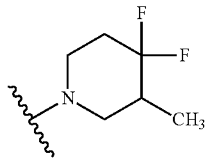 [SMILES: *N1CCC(F)(F)C(C)C1] | 4.74 | $70_{(\pm 14)}$ |
| 18 | 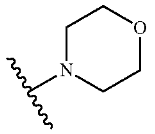 [SMILES: *N1CCOCC1] | 3.08 | >1000 |
| 19 | 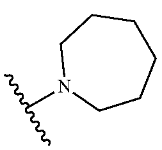 [SMILES: *N1CCCCCC1] | 4.57 | >1000 |
| 20 | 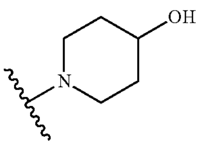 [SMILES: *N1CCC(O)CC1] | 2.61 | >1000 |
| 21 | 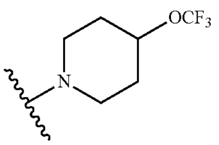 [SMILES: *N1CCC(OC(F)(F)F)CC1] | 4.85 | $135_{(\pm 5)}$ |

[a] $cLogD_{7.4}$ was calculated using ChemAxon MarvinSketch.

[b] To determine $IC_{50}$, MCF-7 cells were incubated with compound for 24 hours and viability measured via alamar blue fluorescence.
Raptinal (100 μM) was used as the 100% dead control.
Data is shown as mean ± s.e.m .;
n ≥ 2 independent replicates.

[c] mixture of diastereomers and their corresponding enantiomers, 4 total compounds.

ErSO-DFP is a Potent ERα-Dependent Anticancer Compound

Figure 2:
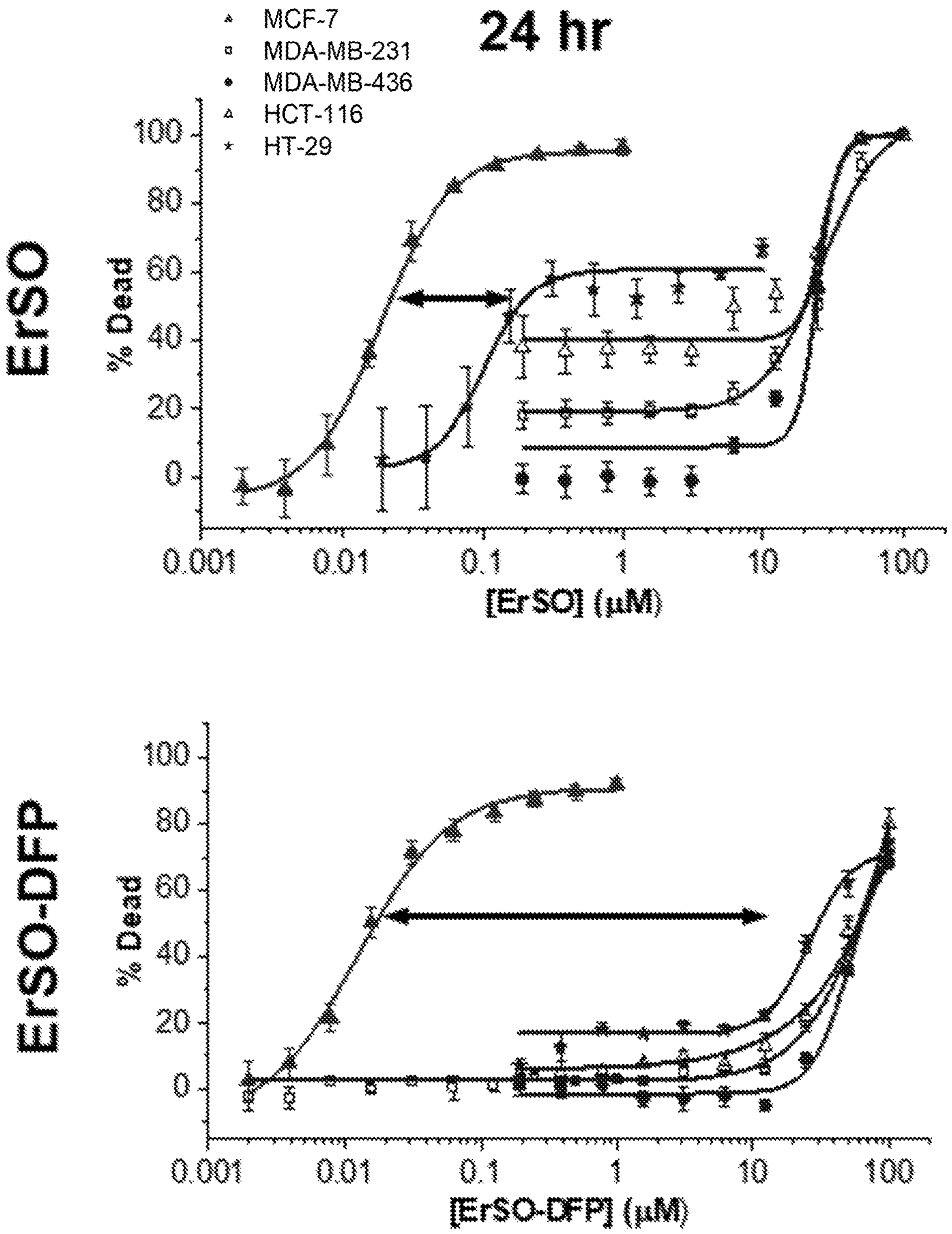
FIG. 2. ErSO-DFP potently kills ERα-positive cancer cell lines with a wider selectivity window than ErSO. $IC_{50}$ curves for ErSO-DFP and ErSO activity against select ERα-positive (red curves) and ERα-negative (blue curves) cancer cell lines. To determine $IC_{50}$, cells were incubated with ErSO for 24 (A) or 72 (B) hours. Viability was measured via alamar blue fluorescence, with raptinal (100 μM) used as the 100% dead control. Data is plotted/expressed as mean±s.e.m.; n≥3 independent replicates. Black double-sided arrow demonstrates the therapeutic window between $IC_{50}$ MCF-7 and select ERα-negative cell lines (Table 3).
Figure 2:
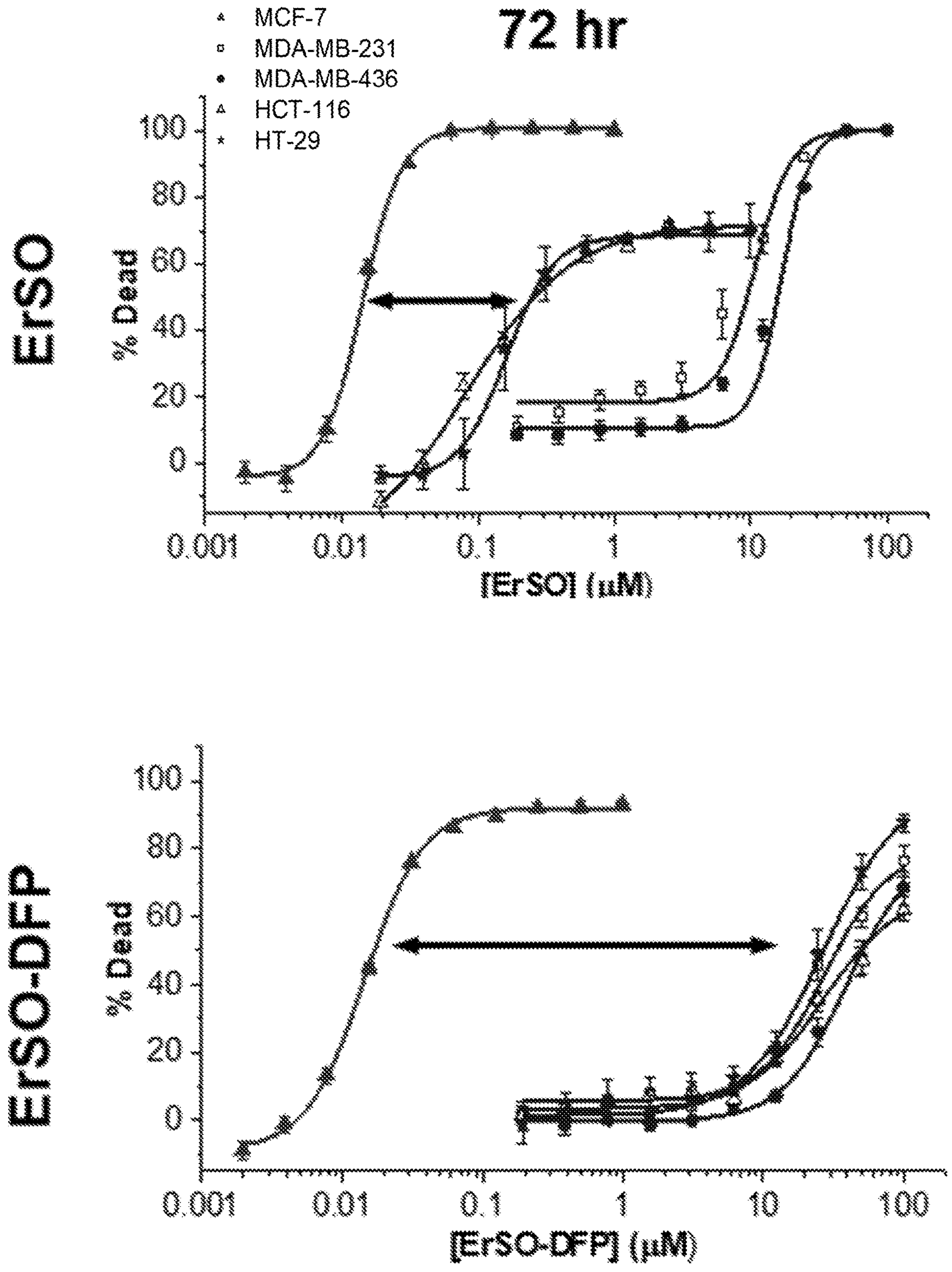

Compound 2 shows significant reduction in lipophilicity relative to ErSO ($cLogD_{7.4}$: 4.37 vs 6.44 respectively) while maintaining activity against MCF-7 cells, warranting in-depth evaluation. Enantiomers of 2 were separated via preparative chiral chromatography and their absolute configurations determined by X-ray crystallography (Chart 2). In accordance with previous observations, the (R)-enantiomer ((R)-2, coined ErSO-DFP) is the active chemical species, approximately twice as potent as the racemic compound; the opposite enantiomer, (S)-2, is devoid of any activity against MCF-7 cells (FIG. 2B). LipE can be a powerful parameter to conveniently track potency and lipophilicity during drug development campaigns. ErSO-DFP has >2.5 fold increase in LipE when compared to ErSO, a shift that is isopotent and a direct result of the decreased lipophilic nature of ErSO-DFP (FIG. 2C).

Chart 2. ErSO-DFP is the active anticancer agent with superior LipE relative to its progenitor, ErSO. Chemical structures of ErSO-DFP and (S)-2 as confirmed by X-Ray crystallography. Physicochemical parameters for ErSO-DFP calculated via ChemAxon MarvinSketch.

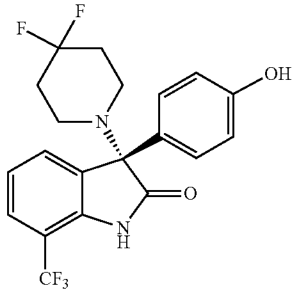

(S)-2

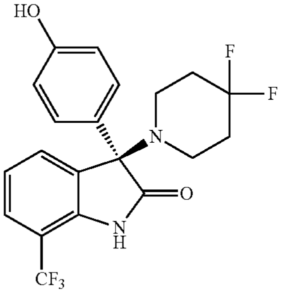

ErSO-DFP (R)-2

ErSO-DFP

| | |
|---|---|
| M.W. | 412.1 |
| $pIC_{50}$ | 7.77 |
| $cLogD_{7.4}$ | 4.37 |
| LipE | 3.40 |
| TPSA | 52.6 |
| clogBB | 0.03 |
| CNS MPO | 3.44 |

Figure 3:
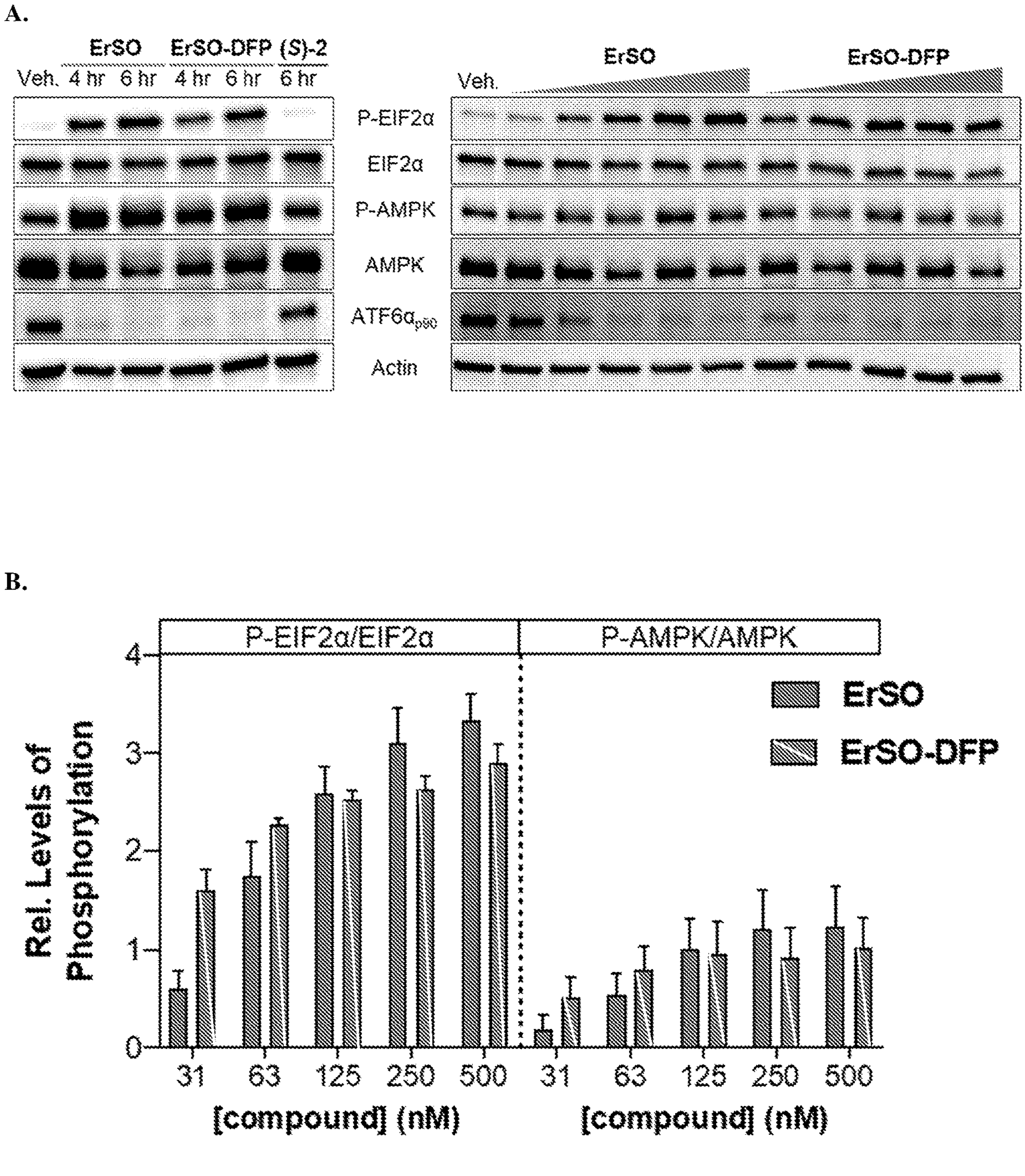
FIG. 3. ErSO-DFP activates the a-UPR in a manner similar to ErSO. MCF-7 cells were incubated with compounds as indicated, harvested, and western blot analysis of key proteins for a-UPR activation conducted. For dose-dependence (blots on the right), cells were incubated for 4 hours with compound (A). Quantification was calculated using ImageJ and the actin bands as loading controls. Data is plotted as mean±s.e.m (B). Blots are representative images of 3 independent replicates.

ErSO-DFP has potent activity, similar to ErSO, against other ERα+ breast cancer cell lines, including the T47D cell line and its therapy-resistant, ERα-mutant versions, T47D-ERaY537S (TYS) and T47D-ERαD538G (TDG) (Table 3). Most critically, evaluation of these compounds against ERα− cell lines shows that ErSO-DFP has notably less ERα-independent activity as compared to ErSO; this effect can be seen in Table 3 and most starkly in the dose response curves in FIG. 3. While ErSO has a time-dependent erosion of ERα-dependent killing in multiple ERα-negative cell lines, most noticeable with HCT-116 and HT-29, ErSO-DFP is inactive ($IC_{50}$>25 μM) in these cell lines at 24 and 72 hours and $IC_{50}$ curves bottom out near 0% cell death in most cases (FIG. 3). For example, with HCT-116 cells, the $IC_{50}$ for ErSO shifts from 11 μM to 0.26 μM and effects bottom out at ~38%. In comparison, the $IC_{50}$ for ErSO-DFP is 55 μM at both 24 and 72 hours, and effects approach 0% at lower concentrations of compound. For ErSO-DFP, there is an average of >2750 fold difference between $IC_{50}$ values (measured at both 24 and 72 hours) observed between ERα+ and ERα− cancer cell lines, a significantly wider therapeutic window for selective cell killing in cell culture relative to ErSO's 555 fold difference.

TABLE 3

Summary of Cellular Potencies of ErSO and ErSO-DFP.

| | | | ErSO | ErSO-DFP |
|---|---|---|---|---|
| | | $cLogD_{7.4}$[a] | 6.44 | 4.37 |
| ERα Positive | MCF-7 | $IC_{50}$ 24 hr (μM) | $0.020_{\pm 0.002}$ | $0.017_{\pm 0.002}$ |
| | | $IC_{50}$ 72 hr (μM) | $0.014_{\pm 0.001}$ | $0.017_{\pm 0.001}$ |
| | | LipE (24 hr) | 1.24 | 3.40 |
| | T47D | $IC_{50}$ 24 hr (μM) | $0.020_{\pm 0.001}$ | $0.016_{\pm 0.002}$ |
| | TYS | $IC_{50}$ 24 hr (μM) | $0.010_{\pm 0.001}$ | $0.007_{\pm 0.001}$ |
| | TDG | $IC_{50}$ 24 hr (μM) | $0.015_{\pm 0.001}$ | $0.009_{\pm 0.001}$ |
| ERα Negative | MDA-MB-231 | $IC_{50}$ 24 hr (μM) | $23_{\pm 3}$ | $55_{\pm 5}$ |
| | | $IC_{50}$ 72 hr (μM) | $8_{\pm 1}$ | $32_{\pm 4}$ |
| | | Fold Change[b] | 571 | 1882 |
| | MDA-MB-436 | $IC_{50}$ 24 hr (μM) | $22_{\pm 1}$ | $64_{\pm 3}$ |
| | | $IC_{50}$ 72 hr (μM) | $14_{\pm 1}$ | $55_{\pm 9}$ |
| | | Fold Change[b] | 1000 | 3235 |
| | HCT-116 | $IC_{50}$ 24 hr (μM) | $11_{\pm 3}$ | $55_{\pm 6}$ |
| | | $IC_{50}$ 72 hr (μM) | $0.26_{\pm 0.03}$ | $55_{\pm 11}$ |
| | | Fold Change[b] | 19 | 3235 |
| | HT-29 | $IC_{50}$ 24 hr (μM) | $0.21_{\pm 0.06}$ | $33_{\pm 4}$ |
| | | $IC_{50}$ 72 hr (μM) | $0.25_{\pm 0.07}$ | $27_{\pm 4}$ |
| | | Fold Change[b] | 18 | 1588 |

To determine $IC_{50}$, cancer cells were incubated with compound for 24 or 72 hours and viability measured via Alamar blue fluorescence.
Raptinal (100 μM) was used as the 100% dead control.
Data is shown as mean ± s.e.m .; n ≥ 3 independent replicates.
[a]$cLogD_{7.4}$ was calculated using ChemAxon MarvinSketch.
[b]Average Fold Change between 24/72 hr $IC_{50}$ values for MCF-7 and ERα negative cell line.

Figure 4:
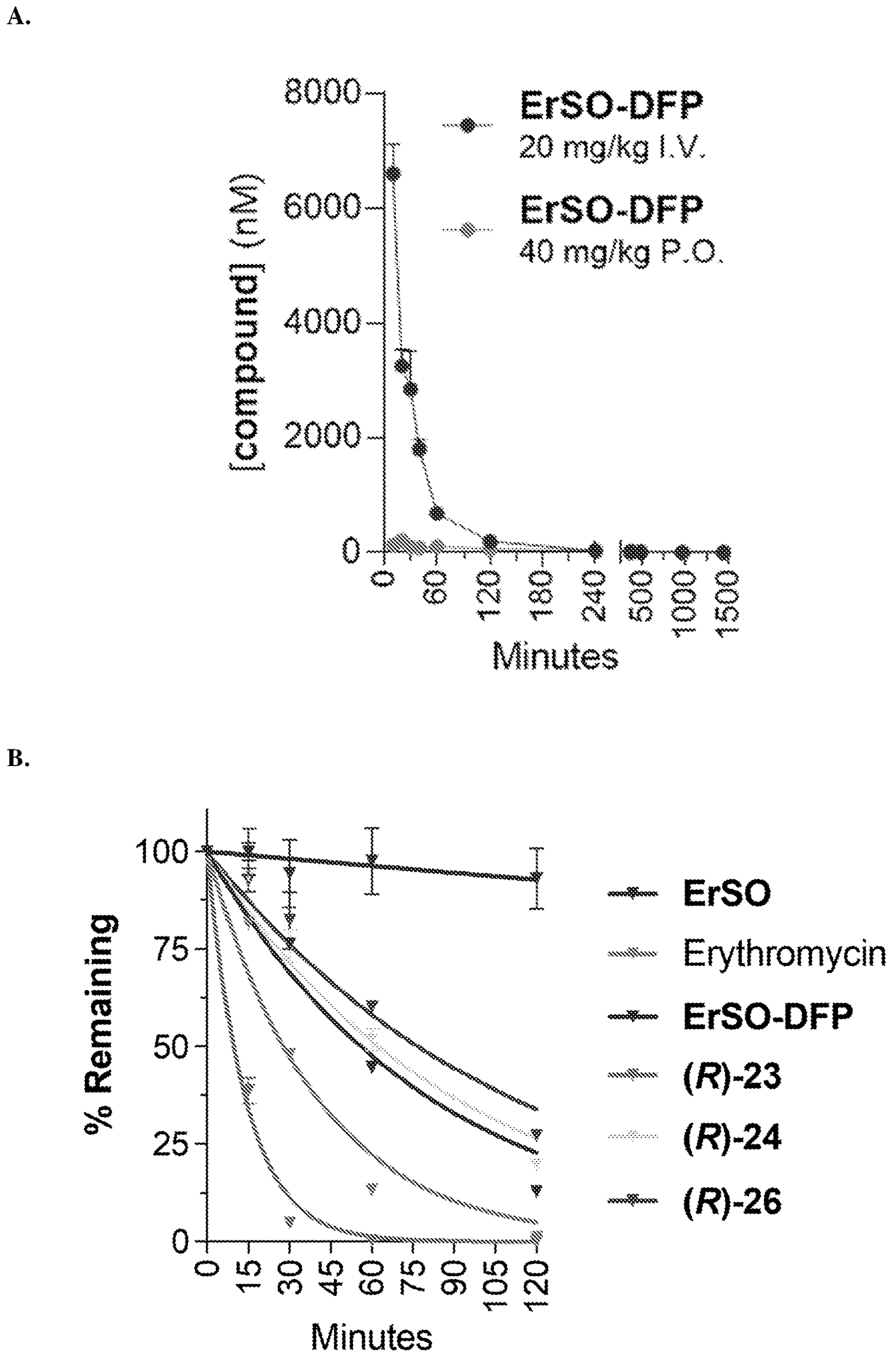
FIG. 4. ErSO-DFP achieves biologically relevant concentrations when dosed intravenously in mice. A, Summary of pharmacokinetic (PK) experiment for ErSO-DFP. Data plotted as mean±s.e.m.; n≥3 mice per time point. B, Simulated gastric fluid (SGF) stability assay results. Compounds of interest (100 μM) were incubated in SGF with pepsin for indicated times, and compound concentration measured by LC-MS/MS. Concentrations were then normalized to t=0 samples and the % remaining calculated and plotted. Half-life ($t_{1/2}$) and curves were calculated with GraphPad PRISM using a one-phase decay equation (Y0=100, Plateau=0, K>0). Erythromycin is a known acid-sensitive, positive control. 95% CI: 95% confidence interval, SD: standard deviation. Data shown is representative of N=2.

ErSO-DFP activates the anticipatory unfolded protein response (a-UPR) in a manner similar to ErSO. To evaluate if ErSO-DFP's anticancer activity is induced through a mechanism similar to ErSO, western blot analysis of key proteins that are consistent with a-UPR activation (appearance of P-AMPK and P-EIF2α, cleavage of ATF6$\alpha_{p90}$) were conducted. In these experiments with MCF-7 cells, ErSO-DFP activates the a-UPR in a time- and concentration-dependent manner similar to ErSO (FIG. 4). No activation of the a-UPR is seen with the inactive enantiomer, compound (S)-2.

Optimized Synthesis of ErSO-DFP

To facilitate further studies, a robust and scalable synthetic route was developed specifically for ErSO-DFP with important modifications from the general route in Scheme 2 and shown specifically for ErSO-DFP in Scheme 3A. The route in Scheme 3A yields usable quantities of material; however, inconsistent yields were observed upon scale-up. Taking inspiration from other work on the synthesis of 3,3-disubstituted oxindoles utilizing heteroatom nucleophiles, we found that employing THF as the solvent (step 1, Scheme 3B) yielded a cleaner tertiary chloride intermediate. Changing to a more basic reaction with excess cesium carbonate in dichloromethane with overnight stirring followed by TBAF deprotection was a highly efficient route to compound 2, produced in 95% yield over 3 steps (Scheme 3B). These optimized conditions appear to be general and preferred for the synthesis of other derivatives in addition to 2 (see methods).

Scheme 3. Optimized Synthesis of ErSO-DFP.

A.

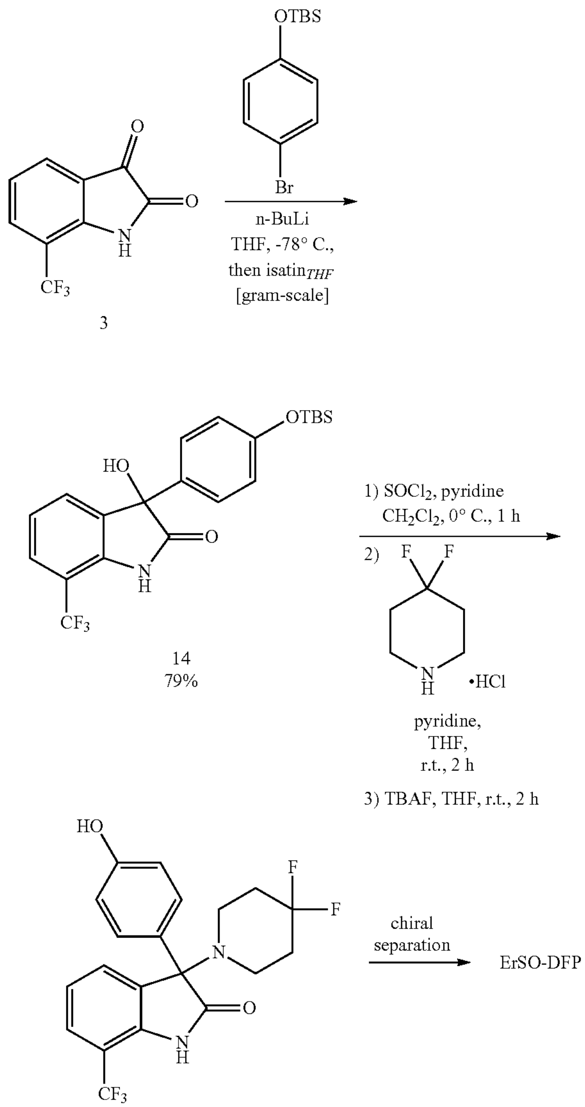

3

14
79%

2
<83%
over 3 steps

B

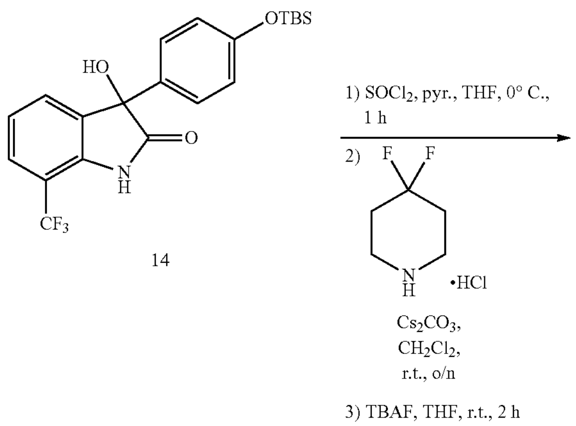

14

-continued

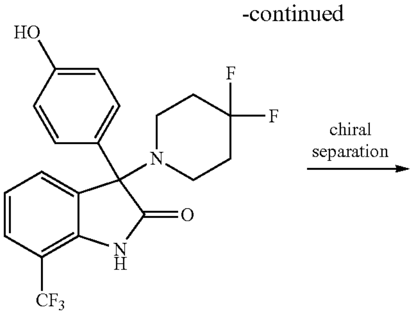

2
95%
over 3 steps

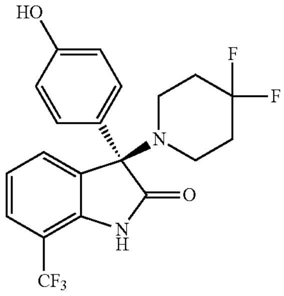

ErSO-DFP

Major changes between the methods are highlighted in blue, n-BuLi: n-butyllithium, isatin$_{THF}$: 7-trifluoromethyl isatin dissolved in THF, $SOCl_2$: thionyl chloride, TBS: tert-butyldimethylsilyl, pyr.: pyridine, chiral separation: fully described in the methods.

Construction and Evaluation of Additional Fluorinated Derivatives

To investigate the unanticipated importance of the difluoropiperdine pharmacophore to the activity of ErSO-DFP, a series of derivatives containing a variety of fluorinated heterocycles (piperidines, pyrrolidines, azetidines) were synthesized, compounds with a cLogD$z_4$ range of 3.50-4.53 (Table 4). Single enantiomers were separated and enantiopure compounds (R)-22-26 were evaluated against an ERα+ breast cancer cell line, MCF-7, and three ERα− cancer cell lines, MDA-MB-231, HCT-116, and HT-29. As shown in Table 4, there is a striking lack of potent activity for compound (R)-22 against MCF-7 cells, suggesting the importance of difluorination for ErSO-DFP's anticancer efficacy. Moving this piperidine difluorination to the 3 position (3,3-difluoropiperidine) subtly decreases activity relative to ErSO-DFP as demonstrated with (R)-23. Contraction of the 6-membered difluoropiperidine to a 5-membered 3,3-difluoropyrrolidine is tolerated, yielding potent derivative (R)-24. Further contraction to the 4-membered 3,3-difluoroazetidine is not well-tolerated as evidenced by the increased $IC_{50}$ of compound (R)-25.

Tetrafluorinated pyrrolidine derivative (R)-26 is the most potent compound with $IC_{50}$ values of 4-5 nM. The opposite enantiomer, compound (S)-26, is inactive against MCF-7 cells, again demonstrating that only one enantiomer in this compound class possesses anticancer activity. Potent derivatives ((R)-23, (R)-24, (R)-276) were further evaluated for their activity against ERα− cancer cell lines MDA-MB-231, HCT-116, and HT-29. Consistent with ErSO-DFP data, compounds (R)-23, (R)-24, and (R)-26 have double-digit micromolar potencies against these cell lines with 24- and 72-hour compound incubations. Compound (R)-26 has the largest fold change (≥3500) and represents the most potent of the fluorinated nitrogen heterocycle containing derivatives. All compounds in this set (ErSO-DFP, (R)-23, (R)-24, and (R)-26) have significant gains in LipE driven by their increased polarity and nanomolar potencies.

TABLE 4

Summary of Biological Activities for Compounds 22-26.

| | | | 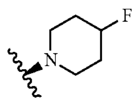 (R)-22 | 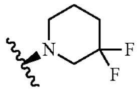 (R)-23 | 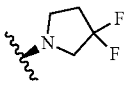 (R)-24 | 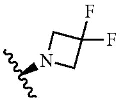 (R)-25 | 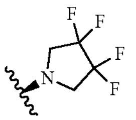 (R)-26 | 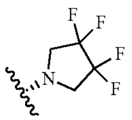 (S)-26 |
|---|---|---|---|---|---|---|---|---|
| | | $cLogD_{7.4}$[a] | 3.50 | 4.18 | 4.10 | 3.83 | 4.53 | 4.53 |
| ERα Positive | MCF-7 | $IC_{50}$ 24 hr (μM) | >1 | $0.039_{\pm 0.01}$ | $0.017_{\pm 0.001}$ | — | $0.005_{\pm 0.001}$ | >1 |
| | | $IC_{50}$ 72 hr (μM) | $0.147_{\pm 0.025}$ | $0.033_{\pm 0.001}$ | $0.022_{\pm 0.001}$ | $0.117_{\pm 0.003}$ | $0.004_{\pm 0.001}$ | >1[c] |
| | | LipE (24 hr) | — | 3.23 | 3.67 | — | 3.77 | — |
| ERα Negative | MDA-MB-231 | $IC_{50}$ 24 hr (μM) | — | $49_{\pm 4}$ | $51_{\pm 5}$ | — | $22_{\pm 2}$ | — |
| | | $IC_{50}$ 72 hr (μM) | — | $22_{\pm 1}$ | $32_{\pm 3}$ | — | $14_{\pm 1}$ | — |
| | | Fold Change[b] | — | 667 | 1455 | — | 3500 | — |
| | HCT-116 | $IC_{50}$ 24 hr (μM) | — | $38_{\pm 4}$ | $45_{\pm 5}$ | — | $24_{\pm 2}$ | — |
| | | $IC_{50}$ 72 hr (μM) | — | $21_{\pm 4}$ | $20_{\pm 6}$ | — | $15_{\pm 3}$ | — |
| | | Fold Change[b] | — | 636 | 909 | — | 3750 | — |
| | HT-29 | $IC_{50}$ 24 hr (μM) | — | $29_{\pm 1}$ | $35_{\pm 6}$ | — | $25_{\pm 1}$ | — |
| | | $IC_{50}$ 72 hr (μM) | — | $25_{\pm 3}$ | $30_{\pm 5}$ | — | $15_{\pm 2}$ | — |
| | | Fold Change[b] | — | 758 | 1364 | — | 3750 | — |

To determine $IC_{50}$, cancer cells were incubated with compound for 24 or 72 hours and viability measured via Alamar blue fluorescence.
Raptinal (100 μM) was used as the 100% dead control. Data is shown as mean ± s.e.m .;
n = 3 independent replicates.
[a]$cLogD_{74}$ was calculated using ChemAxon MarvinSketch.
[b]Average Fold Change between 24/72 hour $IC_{50}$ values for MCF-7 and ERα negative cell line.
[c]n = 2 independent replicates. n.d.: not determined.

ErSO-DFP is Well-Tolerated in Mice and Rats

Figure 5:
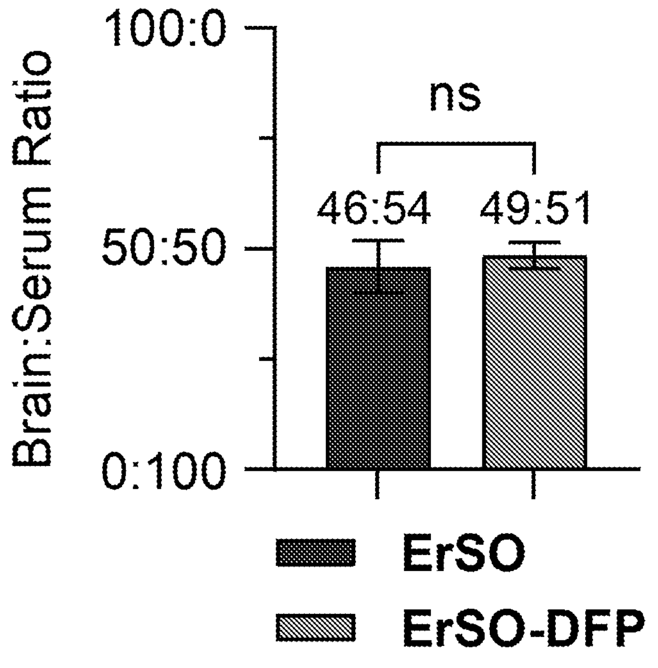
FIG. 5. ErSO-DFP is well-tolerated in vivo and is blood brain-barrier penetrant. B, Mice were treated with 10 mg/kg I.V. of ErSO-DFP or ErSO, following 15 minutes, mice were sacrificed, and their serum and brains collected (n=4 mice per compound). Concentrations of ErSO/ErSO-DFP were determined by LC-MS/MS. The average blood per mouse was approximated as 58.5 mL/kg. Data is plotted as mean±s.e.m. Statistics: two-tailed unequal variance t-test; n.s.: not significant p>0.05 (p=0.7224).

Due to its lack of activity against ERα− cells in culture ($IC_{50}$>25 μM in all ERα− cell lines and time points) and its readily commercially available starting material (i.e., 4,4-difluoropiperidine hydrochloride), ErSO-DFP's in vivo profile was further investigated. ErSO-DFP has significant alterations in hydrophilicity and LipE relative to ErSO (Chart 1, FIG. 2C). The pharmacokinetic (PK) profile in mice and tolerability in mice and rats was investigated for ErSO-DFP. PK assessments revealed that ErSO-DFP (administered intravenously) achieves biologically-relevant concentrations (FIG. 5B), although ErSO-DFP has poor oral availability in mice (F %: 6%). This low F % may be the result of limited acid stability of ErSO-DFP. In a simulated gastric fluid (SGF) stability assay (FIG. 5C, Table 5), ErSO-DFP and compounds (R)-23, (R)-24, (R)-26 had limited stability in SGF with half-lives ranging from 10-77 min. This is in contrast to ErSO's observed (FIG. 5C, Table 5) half-life of >2 hours, consistent with ErSO's % F of 47% in mice. The acid instability of ErSO-DFP may be the result of acid-promoted elimination, a reactivity that is utilized in Friedel-Craft-type reactions to construct 3,3-biaryl derivatives (Scheme 1). To test this hypothesis, compound 2 was subjected to triflic acid and phenol nucleophile. Indeed, Friedel-Craft reaction product 27 was isolated in 20% yield (Chart 3), albeit at longer reaction times and poorer mass balance recovery than those reported with the reaction of compound 3 (Scheme 1). These data provide initial evidence that acid-promoted elimination may be causative of the poor acid stability of ErSO-DFP and derivatives (R)-23, (R)-24, (R)-26 with implications for their oral bioavailability.

TABLE 5

Simulated gastric fluid (SGF) stability assay results.

| Compound | $t_{1/2}$ (min) (95% CI) | % Remaining after 120 min (SD) |
|---|---|---|
| Erythromycin | $28_{(23\text{-}34)}$ | $1_{\pm 1}$ |
| ErSO | >120 | $93_{\pm 1}$ |
| ErSO-DFP | $56_{(43\text{-}73)}$ | $13_{\pm 1}$ |
| (R)-23 | $10_{(8\text{-}11)}$ | $0_{\pm 0}$ |
| (R)-24 | $62_{(53\text{-}74)}$ | $20_{\pm 1}$ |
| (R)-26 | $77_{(66\text{-}91)}$ | $27_{\pm 1}$ |

Compounds of interest (100 μM) were incubated in SGF with pepsin for indicated times, and compound concentration measured by LC-MS/MS.

Concentrations were then normalized to t = 0 samples and the % remaining calculated and plotted.

Half-life ($t_{1/2}$) and curves were calculated with GraphPad PRISM using a one-phase decay equation (Y0 = 100, Plateau = 0, K > 0).

Erythromycin is a known acid-sensitive, positive control.

95% CI: 95% confidence interval,

SD: standard deviation.

Data shown is representative of N = 2.

Chart 3. Summary of reaction of compound 2 with trifilic acid and phenol.

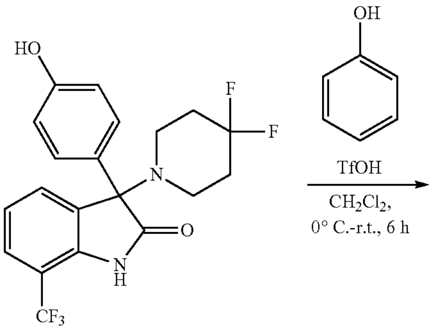

2
36% recovered

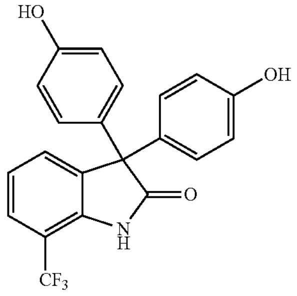

27
20%

Figure 7:
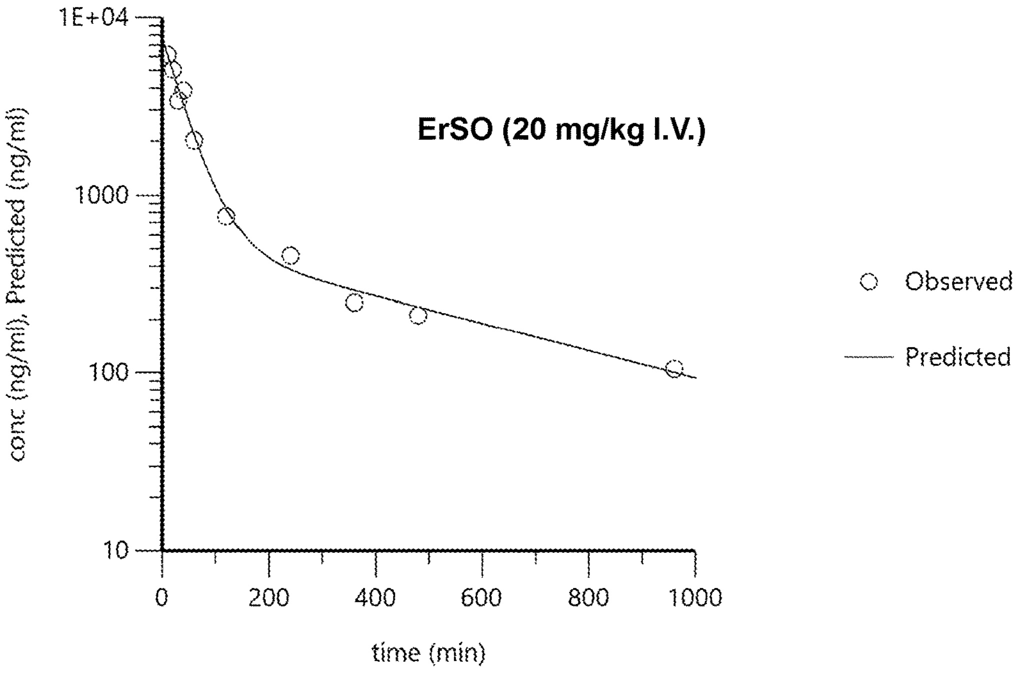
FIG. 7. Graphs showing pharmacokinetics of ErSO at 20 mg/kg I.V (A). and ErSO-DFP at 20 mg/kg I.V (B).
Figure 7:
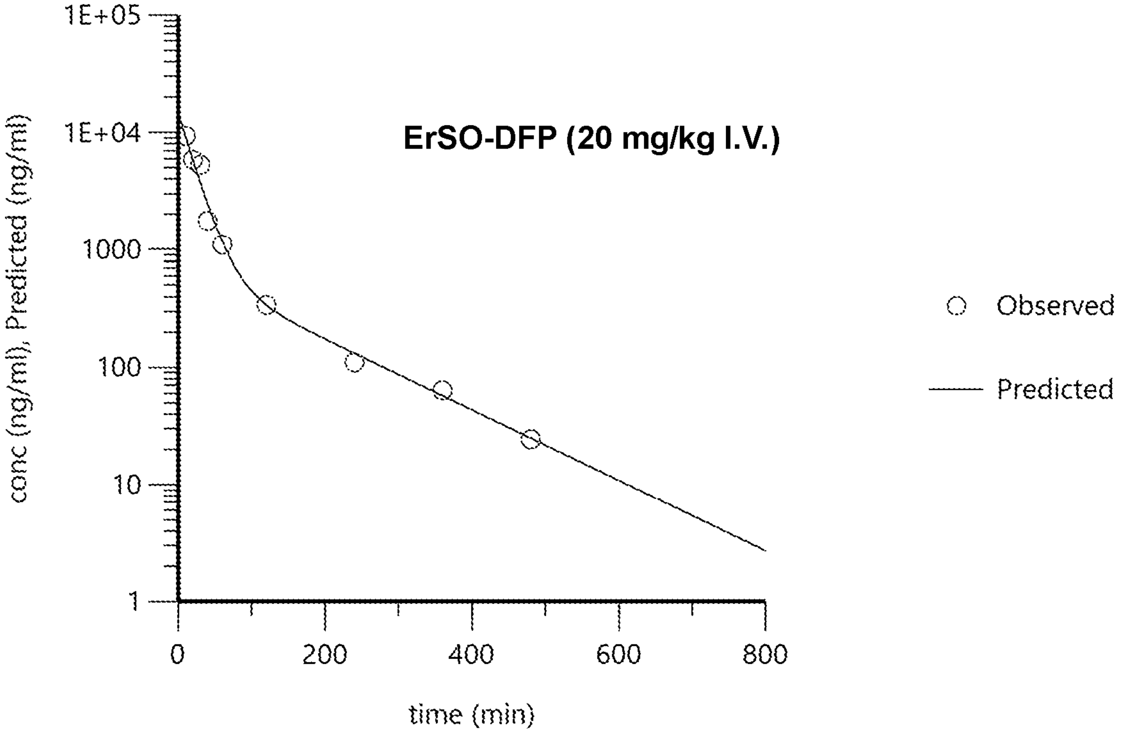

Regardless of its poor oral bioavailability, a head-to-head PK experiment in mice (dosed I.V.) shows that ErSO-DFP $C_{max}$ is approximately double the concentration seen with ErSO, with the AUC~60% of the ErSO value (Table 6, FIG. 7). ErSO-DFP is cleared faster than ErSO with higher clearance values and lower calculated mean-residence times (Table 6, FIG. 7). With this PK data in hand, the maximum tolerated dose (MTD) of ErSO and ErSO-DFP were determined. ErSO-DFP is better tolerated than ErSO in both mice and rats with an almost 5-fold increase in tolerability when administered intravenously; in these experiments, the MTD for intravenously injected ErSO-DFP is 95 mg/kg in mice, and >50 mg/kg in rats (Table 7). Given the similar PK parameters (Table 6), this observed improvement in tolerability of ErSO-DFP relative to ErSO does not appear to be due to a difference in compound exposure.

TABLE 6

Summary of ErSO and ErSO-DFP Pharmacokinetics. I.V. Dosing at 20 mg/kg.

| Parameters | ErSO | ErSO-DFP | ErSO-DFP:ErSO |
|---|---|---|---|
| $C_{max}$ (ng/mL) | 7712 | 14656 | 1.9 |
| AUC (h * ng/mL) | 10127 | 6374 | 0.6 |
| MRT (h) | 5.1 | 0.88 | 0.2 |
| CL (mL/min/kg) | 33 | 52 | 1.6 |
| $V_{ss}$ (mL/kg) | 10161 | 2754 | 0.3 |

Figure 6:
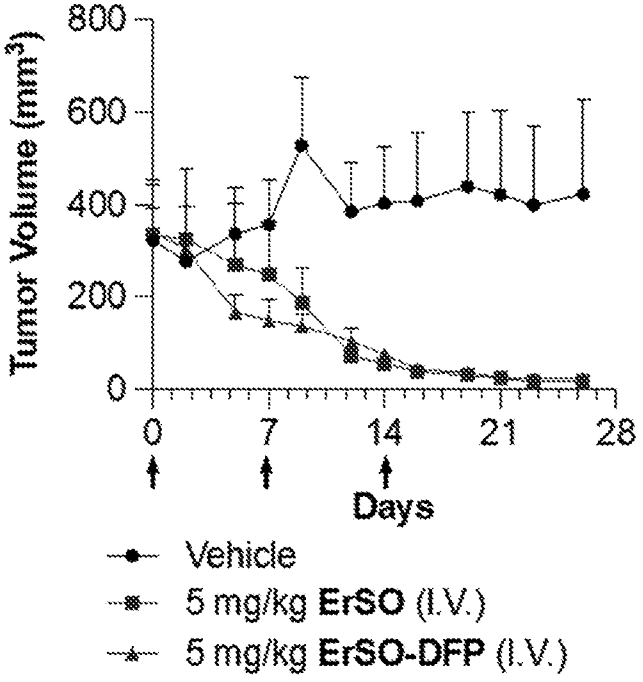
FIG. 6. ErSO-DFP treatment leads to profound tumor regression at a low dose, which coupled with the high MTD, suggests it as a compound with a large therapeutic index. A, ErSO-DFP regresses MCF-7 tumors in a similar manner as ErSO. MCF-7 cells ($5\times10^6$) were injected into the mammary fat pad of ovariectomized Nu/J mice supplemented with a 60-day E2 pellet (0.36 mg) and resulting tumors grown to an average size of >300 $mm^3$. Groups were then treated once-a-week for 3 total doses (i.e., 3×q.wk.) with I.V. administration; n=6 for each treatment group. Mice were not treated after Day 14. B, Summary of percent change in mouse weight observed during MCF-7 orthotopic study shown in A. No weight changes were statically significant from each other at any time point (n.s., p value>0.05) as determined by a two-way ANOVA; n=6 for each treatment group.
Figure 6:
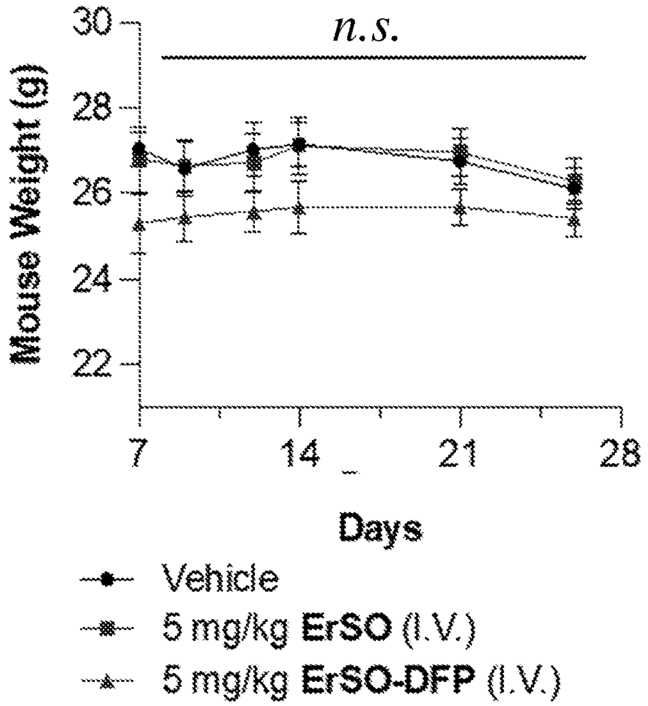

ErSO-DFP has different predicted brain penetrance relative to ErSO, cLogBB of 0.03 and 0.25 respectively and CNS MPO scores of 3.44 to 2.83 respectively. The brain-to-serum ratio of ErSO-DFP was measured experimentally through a 10 mg/kg intravenous injection in mice. Contrary to cLogBB prediction and CNS MPO scores which predict a difference, ErSO-DFP maintains similar blood-brain partitioning ratios as ErSO (FIG. 6B), suggesting that the increased tolerability of ErSO-DFP is not the result of poor BBB penetration. In summary, these data demonstrate that ErSO-DFP, when dosed intravenously, reaches significant, therapeutically relevant concentrations in vivo, and is better tolerated than ErSO.

TABLE 7

Summary of maximum tolerated dose (MTD) experiments with ErSO-DFP and ErSO.

| | Organism | | | | | |
|---|---|---|---|---|---|---|
| | Mouse | | | | Rat | |
| | Administration | | | | | |
| | P.O. | | I.V. | | I.V. | I.V. |
| | Compound | | | | | |
| | ErSO | ErSO-DFP | ErSO | ErSO-DFP | ErSO | ErSO-DFP |
| MTD (mg/kg) | >150[a] | >200 | 20 | 95 | 10-15 | >50 |
| Fold Increase Rel. to ErSO | | — | | 4.8 | | 3.3-5 |

MTD's were determined with n ≥ 2, single dose.

[a]Reported by Boudreau, M. W.; et al. *Sci. Transl. Med.* 2021, 13, eabf1383.

ErSO-DFP Maintains ErSO-Like Activity in a Mouse Model of ERα-Positive Breast Cancer The significant antitumor effect of ErSO treatment on ERα+ breast tumors suggests its potential in selective anticancer therapy; this type of rapid and dramatic tumor regression is not seen in murine tumor models using conventional selective estrogen receptor degraders/downregulators (SERDs) and selective estrogen receptor modulators (SERMs). To assess the antitumor effect of ErSO-DFP, mice bearing large (average size>300 $mm^3$ prior to treatment) MCF-7 tumors were treated with ErSO or ErSO-DFP once-a-week for three total doses (I.V. administration at 5 mg/kg). ErSO-DFP treatment leads to profound regression of MCF-7 tumors, mirroring results with the ErSO-treated mice (FIG. 7A). Treatments were well-tolerated, and no significant weight change was observed throughout the study (FIG. 7B). Using this initial efficacy data combined with head-to-head MTD studies (Table 7), it is clear that the therapeutic index (TI) for ErSO-DFP is greater than ErSO, likely a ~5-fold or greater increase. Further dose finding experiments with ErSO-DFP are necessary to fully establish a TI value.

Discussion

While endocrine therapy has substantially improved the five-year survival rates for patients with ERα+ breast cancer, there is still an acute need for the treatment of drug resistant, advanced ERα+ breast cancers. There are numerous examples of new therapies seeking to address this need, including novel next-generation SERDs and ERα-targeting proteolysis targeting chimeras (PROTACs). However, these endocrine therapies utilize known inhibitory mechanisms that induce cancer cell cytostasis and lead to only limited tumor regression in preclinical models. This challenge is exemplified by the recently reported next-generation SERD, GDC-9545 (giredestrant) that has potent antiproliferative activity in cell culture but fails to quantitatively regress highly estrogen-dependent MCF-7 tumors, even in combination with CDK4/6 inhibitor palbociclib. The slow tumor regression induced by these drugs has implications for clinical applications, including the avoidance of using endocrine therapies in patients with large tumor burdens and significant toxicities upon long-term endocrine therapy treatment leading to the well-reported problem of poor patient compliance.

In contrast to the cytostatic activities of endocrine therapies, a-UPR activators have the potential to be highly effective, fast-acting, cytotoxic ERα-dependent therapies. ErSO-DFP and ErSO are members of the substituted 3-(4-hydroxyphenyl)indoline-2-one class of anticancer small molecules. A well-known member of this class is oxyphenisatin, a laxative used for over 40 years which later was shown to have antiproliferative effects against transformed and cancer cells. Derivatives of oxyphenisatin have potent anticancer activity. For example, Andruska et al (*Proc. Natl. Acad. Sci. USA,* 2015, 112 (15), 4737) disclosed BHPI, an oxyphenisatin derivative that retards the growth of ERα+ cancer cells through hyperactivation of ERα-mediated a-UPR. Initial demonstrations of the a-UPR's 'druggability' with BHPI was the basis for the discovery of ErSO, a compound that induces stark and unique cytotoxic a-UPR hyperactivation. While progenitor a-UPR activator BHPI is cytostatic against most ERα+ cancer cell lines, ErSO is rapidly cytotoxic and induces quantitative tumor regression in preclinical tumor models as a single agent with once-a-week dosing. ErSO-DFP displays a similar antitumor activity to ErSO with significant tumor regressions observed with once-a-week intravenous dosing and has an even wider therapeutic window than ErSO. The exact molecular underpinnings for this switch between a cytostatic or a cytotoxic a-UPR activator are yet to elucidated, but the altered phenotype and tumor regressions are clear.

General lipophilicity (predicted by $cLogD_{7.4}$) can have major implications for a compound's selectivity and idiosyncratic toxicity profile. While lipophilicity can be critical for high affinity ligands and on-target mechanism of action, too much lipophilicity may lead to narrowed therapeutic windows driven by off-target mechanisms and other liabilities. ErSO's poor lipophilic efficiency (LipE=1.26) may play a role in the observed erosion of ERα-dependent activity in cell culture. Supporting this assertion that excessive lipophilicity may be problematic for selectivity, ErSO-DFP and other more polar compounds ((R)-23, (R)-24, (R)-26) maintain robust selectivity against ERα+ and ERα− cancer cell lines even with 72-hour incubations. This selectivity in cell culture appears to also translate into better tolerability in vivo, as shown with ErSO-DFP.

As previously reported with ErSO, 3-(4-hydroxyphenyl) indoline-2-ones can suffer from rat speciation toxicity. The exact underlying pharmacologic explanation and human relevance of this toxicity is not known. However, when considering tolerability the multi-year clinical use of oxyphenisatin is encouraging; while this drug was ultimately withdrawn from the clinic due to a rare hepatotoxicity that is untenable for a laxative drug, it was widely prescribed for four decades. Regardless, this rat toxicity can be used as a key preclinical filter for this drug class. Outside of simple cycloalkane substitutions, there has only been a limited set of substitutions to diversify 3-(4-hydroxyphenyl)indoline-2-ones. To optimize lipophilic efficiencies, cancer cell line specificity, and rat in vivo tolerability, we developed a highly modular strategy to access a variety of diverse polar derivatives of this class. Beyond ErSO-DFP and derivatives herein, this synthetic route can be utilized in future optimizations to expand the SAR and further modulate desirable parameters (e.g. oral bioavailability). As demonstrated by ErSO-DFP, prioritization of ligand lipophilic efficiency and cancer cell selectivity in culture should lead to compounds with gains in in vivo tolerability in mice and rats, defining a powerful optimization strategy for on-going and future a-UPR activator medicinal chemistry campaigns.

The profound antitumor effects seen with a-UPR activators warrants their further investigation with a specific need to delineate direct target engagement and other aspects of their underlying mechanism. ErSO's apparent ERα-independent effects, in some cancer cell lines when assessed at longer compound incubation times, may complicate studies surrounding target engagement, a-UPR activation, and cancer cell death. To this end, ErSO-DFP and its derivatives (e.g. (R)-26) are more ideal chemical probes for studying a-UPR activation as exemplified by their striking inactivity in ERα− cancer cell lines.

The strong necessity for difluorination to the activity of ErSO-DFP was an unexpected finding of this study. Fluorine atoms can have profound effects on a ligand's physiochemical and confirmational properties and contribute to a variety of interactions between ligands and their protein target. Indeed, fluorination of nitrogen heterocycles utilized herein does decrease the predicted pKa of the corresponding conjugate acid and that pKa perturbation may be a factor in their potent activity. Further, fluorination of piperidines (and other heterocycles) can have significant effects on compound conformation and may alter the dominate conformer in solution and/or in target binding. The exact driving force for the potent biological activity of ErSO-DFP compared to compounds lacking this difluorination (e.g., 16) remains unknown. The crucial role of fluorination in the development of a variety of drug-like ligands is clear, and ErSO-DFP and related compounds are another example of this essentiality.

In summary, using lipophilicity-directed design, we report the discovery of ErSO-DFP and related derivatives that exhibit potent and selective ERα-dependent anticancer activity. ErSO-DFP preserves many of the positive features of its progenitor ErSO, namely potent $ER\alpha^{WT/Mutant}$-dependent a-UPR activation and cancer cell death. Excitingly, while more polar, ErSO-DFP still maintains BBB penetration, opening the door for future development for the treatment of drug-resistant, $ER\alpha^{WT/Mutant}$-positive, brain metastases. ErSO-DFP and other compounds reported herein are promising toward the development of a-UPR activators for the treatment advanced ERα+ breast cancer and other ERα+ cancers.

General Synthetic Methods

The invention also relates to methods of making the compounds and compositions of the invention. The compounds and compositions can be prepared by any of the applicable techniques of organic synthesis, for example, the techniques described hereinbelow (Example 2). Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure,* $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T.

W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 2 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g., inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl protecting groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable heteroatom protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e., routes or methods to prepare the compounds by the methods of the invention. For the most part the decision as to which groups to protect, when to do so, and the nature of the chemical protecting group ("PG" or "P") will be dependent upon the chemistry of the reaction to be protected against (e.g., acidic, basic, oxidative, reductive, or other conditions) and the intended direction of the synthesis.

The preparation of compounds of the invention are described in the Examples below. As would be readily recognized by one of skill in the art, various other compounds of the formulas described herein can be prepared by using the appropriate commercially available or readily prepared starting materials and/or by installing substituents during synthesis of the target compound. Preparation of certain relevant starting materials has been described in International Publication No. WO 2020/009958 (Shapiro et al.), which applications are incorporated herein by reference.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations such as multiple inhalations from an insufflator or by application of a plurality of drops into the eye.

The compounds described herein can be effective antitumor agents and have higher potency and/or reduced toxicity as compared to BHPI. Preferably, compounds of the invention are more potent and less toxic than BHPI, and/or avoid a potential site of catabolic metabolism encountered with BHPI, i.e., have a different metabolic profile than BHPI. Furthermore, the compounds described herein cause less severe ataxia than BHPI and other known compounds.

The invention provides therapeutic methods of treating cancer in a vertebrate such as a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any of the various type of malignant neoplasm, which are in general characterized by an undesirable cellular proliferation, e.g., unregulated growth, lack of differentiation, local tissue invasion, and metastasis. Cancers that can be treated by a compound described herein include, for example, breast cancer, cervical carcinoma, colon cancer, endometrial cancer, leukemia, lung cancer, melanoma, pancreatic cancer, prostate cancer, ovarian cancer, or uterine cancer, and in particular, any cancer that is ERα positive.

The ability of a compound of the invention to treat cancer may be determined by using assays well known to the art. For example, the design of treatment protocols, toxicity evaluation, data analysis, quantification of tumor cell kills, and the biological significance of the use of transplantable tumor screens are known. In addition, ability of a compound to treat cancer may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Biological Procedures

Cancer Cell Lines: Culturing Conditions and Validation. All cell lines were cultured at 37° C. with 5% $CO_2$. All ERα-positive cell lines were grown in media lacking phenol red. MCF-7 were grown in EMEM with 10% FBS and 1% penicillin-streptomycin (P/S). T47D were cultured in MEM with 10% FBS and 1% P/S. TYS and TDG cells were grown in MEM supplemented with 10% CD-FBS and 1% P/S. HCT-116 and MDA-MB-231 cells were cultured in RPMI-1640 supplemented with 10% FBS and 1% P/S. MDA-MB-436 cells were cultured in DMEM supplemented with 10% FBS and 1% P/S. HT-29 were cultured in McCoy's media supplemented with 10% FBS and 1% P/S. All cell lines were used directly from ATCC stocks and/or have been further authenticated using PowerPlex16HS Assay (Promega) as described previously.[54] In short, >1 million cells were harvested and lysed using the cell lysis buffer (50 mM Tris, 50 mM EDTA, 25 mM sucrose, 100 mM NaCl, 1% SDS, pH 8). DNA extraction and short tandem repeats (STRs) profiling for each cell line were carried out at the University of Arizona Genetics Core (UAGC). Autosomal STR profiles were compared to reference databases such as ATCC, DSMZ, and JCRB.

Alamar Blue Fluorescence for Anticancer Activity ($IC_{50}$). 2,000-15,000 cells per well were seeded a 96-well plate. Cells were allowed to adhere before DMSO stock solutions of test compounds were added to each well with a final concentration of DMSO in each well=1%; final volume: 100 μL. At the end of the desired incubation time (e.g., 24 or 72 hours), media in each well was aspirated and new fresh media (no compound, 100 μL) was added. Alamar blue solution (4 mg resazurin per 40 mL PBS) was then added (10 μL). After 2-6 hours incubation, each well's fluorescence ($\lambda_{excit.}$=555 nm, $\lambda_{emission.}$=585 nm) was measured using a SpectraMax M3 plate reader (Molecular Devices). Percent dead was determined by comparison to a 100% dead control: 100 μM raptinal treated cells. Dose dependent curves and $IC_{50}$ were calculated using Origin Pro V10.

a-UPR Immunoblotting/Western Blot Procedure. 400,000 MCF-7 cells/per well were seeded into 6 or 12 well plates and allowed to adhere overnight. Media was then aspirated from each well and then fresh media with diluted test compound (0.1% DMSO concentration) was added accordingly. Cells were incubated for 4 or 6 hours, then harvested. PBS-washed cell pellets were then lysed using RIPA buffer containing phosphatase (BioVision) and protease inhibitor cocktail (Calbiochem). Protein concentrations were determined using the BCA assay (Pierce). Lysates containing 10-15 μg of protein were loaded onto 4-20% gradient gels (BioRad), and SDS-PAGE was run. Proteins were then transferred onto membrane (PDVF Millipore) and blots blocked with BSA solution (2 g in 40 mL TBST) for one hour. After blocking, primary antibody was added and incubated overnight (using manufacturer's recommended dilutions). Following overnight incubation, blots were washed with TBST (5-minute incubation for each wash, washed 3 times), then incubated with HRP-linked secondary antibody for 1 hour in TBST. Blots were washed (10-minute incubation for each wash for a total of two ten-minute washes). SuperSignal West Pico Solution was then added following manufacturer's procedures and blots imaged with ChemiDoc.

Antibodies. Antibodies used: Phospho-AMPK (Thr172): CST-2535, AMPK: CST-5832, Phospho-EIF2α (Ser51): CST-3398, EIF2α: CST-5324, ATF6α: CST-65880, β-actin-HRP conjugate: CST-5125, β-actin: CST-4970, Anti-rabbit IgG HRP-linked: CST-7074.

IACUC Guidelines and Protocol Numbers. All in vivo work was conducted in accordance with UIUC IACUC guidelines and approved protocols (IACUC protocol: 18075).

Pharmacokinetic (PK) Studies. Female CD-1 mice (Charles River, ~25 g mice) were administered compounds (i.e., ErSO or ErSO-DFP) either intravenously (I.V. tail vein) or oral gavage (P.O.) at 20 mg/kg or 40 mg/kg as indicated. Mice were then sacrificed in cohorts of 3 at time points (#, #, #). Blood was collected, centrifuged, and plasma separated for quantification of test compound utilizing LC-MS/MS (UIUC Metabolomics Center, Urbana, IL.). Determined compound concentration was then analyzed using non-linear regression programing (WinNonlin) and pharmacokinetic parameters estimated.

Simulated Gastric Fluid (SGF) Stability Assay. SGF was prepared fresh by adding 3.2 g pepsin (Sigma Aldrich P7000) to 1000 mL of SGF (Fischer Scientific 7108-16) and the pH adjusted to 1.2 using a pH meter. This $SGF_{with\ pepsin}$ solution was then warmed to 37° C. 990 μL of warmed $SGF_{with\ pepsin}$ was then aliquoted into multiple Eppendorf tubes, followed by 10 μL of 10 mM DMSO stock solutions of test compounds. Erythromycin (MedChemExpress HY-B0220) is a positive control for this stability assay. Samples were incubated at 37° C. for the entire experiment with vortexing every 15 minutes. At each desired time point (0, 15, 30, 60, 120 minutes), a 100 μL aliquot is removed and quenched into 50 μL of acetonitrile. Samples are stored at 4° C. until all time points are complete. Samples were then vortexed and then clarified at 3,000 RPM for 10 minutes in a 4° C. centrifuge. Supernatants were collected and compound concentrations determined by LC-MS/MS (UIUC Metabolomics Center, Urbana, IL.). Determined compound concentrations were used to calculate percent remaining compared to t=0 samples. A single-phase exponential decay equation was fitted to the data for each compound using GraphPad software (one-phase decay equation, Y0=100, Plateau=0, K>0) and half-life ($t_{1/2}$) was calculated using these fitted equations.

Maximum Tolerated Dose (MTD) Experiments in Mice and Rats. Female CD-1 mice (Charles River, 7-8 weeks old) or CD Sprague Dawley IGS rats (Charles River, 250-350 g) were treated with ErSO or ErSO-DFP at the desired dose either intravenously (I.V. tail vein) or oral gavage (P.O.). Rodents were monitored for signs of distress, lethargy, neurotoxicity, and so forth for multiple days after compound administration. If a given dose was tolerated, higher doses were investigated until an intolerable dose was observed (often associated with acute signs of toxicity and/or lethality) or the solubility limit was reached with a given test compound. The MTD was defined as the maximum dose in which any acute side effects observed were tolerated and no lethality observed.

MCF-7 Orthotopic Tumor Model. Nu/J ovariectomized mice (Jackson's lab) were supplemented with a 60-day E2 pellet (0.36 mg, Innovative Research of America) 2-3 days prior to tumor cell inoculation. MCF-7 cells ($5\times10^6$, in 1:1 HBSS:matrigel) were inoculated into the mammary fat pad and allowed to establish and tumors grown to ~300-400 $mm^3$ (~21-28 days to establish). ErSO and ErSO-DFP were formulated in 5% DMSO, 10% Tween-20, and 85% PBS. Mice were then randomized (n=6 per group), and intravenously (I.V. tail-vein) injected with vehicle (5% DMSO, 10% Tween-20, 85% PBS), ErSO (5 mg/kg), or ErSO-DFP (5 mg/kg) once-a-week for three total doses (day 0, day 7, day 14). Tumor size was measured by caliper, and mouse weights were recorded.

BBB Penetrance Study. CD-1 mice (Charles River) were injected with ErSO or ErSO-DFP intravenously (I.V., tail vein) at doses indicated and sacrificed 15 minutes after injection (n=3 for each time point and dose). Mice were sacrificed and blood collected. Residual circulatory volume was removed via perfusion. Blood samples were centrifuged at 13,000 RCF for five minutes. The resulting supernatant was collected and stored at −80° C. prior to analysis. Brains were harvested from the cranial vault, weighed, and flash frozen with liquid nitrogen. 1000 μL of cold methanol was added to thawed brains and then brains were homogenized using a handheld tissue homogenizer. The resultant slurry was centrifuged twice at 13,000 RCF for 10 minutes per run and the supernatant was collected and frozen at −80° C. prior to analysis. Samples were then analyzed by LC-MS/MS (Metabolomics Laboratory of the Roy J Carver Biotechnology Center UIUC) to determine ErSO or ErSO-DFP concentration in both serum and brain. To calculate absolute brain:serum ratios, an approximated mouse blood volume of 58.5 mL/kg was utilized for each mouse.

Example 2. Materials and Methods for Chemical Synthesis

General methods. All reactions described herein were conducted under inert atmosphere (i.e., argon gas) unless otherwise noted. Chemical reagents were purchased from commercial sources and used without further purification. 7-trifluoroisatin (1) is commercially available (e.g., Oakwood Chemical-024866). All solvents used were anhydrous, either bought from commercial sources or resulting from being passed through activated alumina columns utilizing a PureSolv MD-5 solvent purification system. Final compounds were dried via overnight lyophilization from neat acetonitrile. $^1H$ NMR, $^{13}C$ NMR, $^{19}F$ NMR experiments were conducted on a Bruker Avance III HD 500 MHz NMR with a CryoProbe. Spectra obtained in $CD_3OD$ were referenced for 3.31 ppm and 49.00 ppm for $^1H$ and $^{13}C$ NMR spectra respectively. For $^{19}F$ NMR, references from a corresponding $^1H$ NMR experiment was utilized. All NMR chemical shifts are reported in ppm (δ), coupling constants (J, Hz), and peaks reported as: s=singlet, bs=broad singlet, d=doublet, t=triplet, q=quartet, m=multiplet. $^{13}C$ and $^{19}F$ peak multiplicities are all singlets unless otherwise noted with the same designation used for $^1H$ NMR. High resolution mass spectra (HRMS) were obtained at the UIUC SCS Mass Spectrometry Laboratory utilizing electrospray ionization (ESI). X-Ray crystallography was conducted at UIUC SCS George L. Clark X-Ray Facility utilizing a Bruker D8 Venture Duo instrument which can determine absolute stereochemistry. Further crystallographic information is available upon request and has been deposited on Reciprocal Net. The >95% purity of compounds utilized in biological assays was determined using HPLC at λ: 254 nm. Chiral HPLC will often show two peaks for racemic mixtures, an important consideration for compounds herein since often only one enantiomer for this class of compounds herein show biological activity. For a few compounds (denoted throughout), resolution of both enantiomers was not achieved with the HPLC chiral column used.

Synthesis of 1, ErSO, (R)-3-(4-hydroxyphenyl)-3-(4-(trifluoromethoxy)phenyl)-7-(trifluoromethyl)indolin-2-one. Compound 1 was synthesized and isolated as reported (Sci. Transl. Med., 2021, 13, 603). $^1H$ NMR ($CD_3OD$, 500 MHz) δ: 7.53 (d, J=8.0 Hz, 1H), 7.45 (d, J=7.5 Hz, 1H), 7.31 (d, J=8.9 Hz, 2H), 7.25-7.14 (m, 3H), 7.03 (d, J=8.8 Hz, 2H), 6.74 (d, J=8.9 Hz, 2H). $^{19}F$ NMR ($CD_3OD$, 471 MHz) δ: −59.48, −62.98. Melting Point: 91.1-94.8° C.

Synthesis of 4, 3-hydroxy-3-(4-(trifluoromethoxy)phenyl)-7-(trifluoromethyl)indolin-2-one. A flame-dried round bottom flask under inert atmosphere was charged with 1-bromo-4-(trifluoromethoxy)benzene (23.30 mmol, 3.5 mL) and dissolved in THF (23 mL). The reaction mixture was cooled to −78° C. and a solution of n-BuLi (21.39 mmol, 14.3 mL) added dropwise over 10 minutes. The reaction was stirred for 1 hour at −78° C. In another flame-dried flask, 7-(trifluoromethyl)indoline-2,3-dione (9.30 mmol, 2.0 g) was added and dissolved in THF (23 mL) under inert atmosphere. This solution of isatin at room temperature was added to the reaction vessel at −78° C. dropwise over 15 minutes. The resultant mixture was stirred at −78° C. for 1 hour, removed from the cold bath, allowed warmed to room temperature while stirring for 30 minutes. The reaction was quenched with water (15 mL). The solution was poured into a separatory funnel with 100 mL EtOAc and 100 mL of 1:1 $H_2O$:Saturated Brine. The organics were extracted with ethyl acetate (3×, −50-100 mL) and the combined organic layers washed with brine, then dried over sodium sulfate, filtered, and concentrated in vacuo. The resultant oil was purified via automated flash chromatography ($SiO_2$, eluting solvent: initial mixture 0:100 Ethyl Acetate:Hexanes with increasing gradient to 50:50 Ethyl Acetate:Hexanes over 18 column volumes). 4 was isolated in 65% yield as an off-white/yellow solid (6.07 mmol, 2.29 g). $^1H$ NMR ($CD_3OD$, 500 MHz) δ: 7.57 (d, J=8.0 Hz, 1H), 7.47 (d, J=8.8 Hz, 2H), 7.41 (d, J=7.4 Hz, 1H), 7.25 (d, J=8.5 Hz, 2H), 7.20 (t, J=7.8 Hz, 1H). $^{13}C$ NMR ($CD_3OD$, 126 MHz) δ: 182.08, 150.31 (q, J=1.7 Hz), 140.70 (q, J=2.28 Hz), 140.54, 135.70, 129.90, 128.61, 127.35 (q, J=4.5 Hz), 125.09 (q, J=270.9 Hz), 124.04, 122.01, 121.88 (q, J=255.7 Hz), 113.84 (q, J=33.3 Hz), 77.09. $^{19}F$ NMR ($CD_3OD$, 471 MHz) δ: −60.23 (s), −63.71 (s). HRMS (ESI): m/z calc. for $C_{16}H_8NO_3F_6$ $[M+H]^+$ 376.0408, found: 376.0404. Melting Point: 59.5-61.8° C.

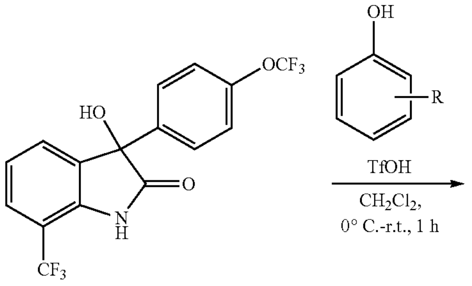

4
65%

-continued

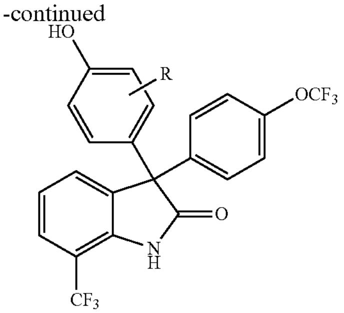

5-13
36-91%

General Procedure A (Compounds 5-13). A round bottom flask was charged with compound 4 (1.06 mmol, 0.40 g) and phenol of interest (3.71 mmol) were dissolved in dichloromethane (2.2 mL). The reaction mixture was then placed in an ice bath and triflic acid (TfOH, 0.4 mL) was then added dropwise. Caution: Triflic acid dissolves many common plastics, especially plungers of syringes, so using metal needles or glass syringes are recommended. If using a plastic syringe, avoid contact with the plunger of the syringe. The reaction vessel was then removed from the ice bath (or ice was allowed to melt) and stirred at room temperature for 1 hour. The reaction mixture was then poured into ice-filled saturated sodium bicarbonate (aqueous, −50 mL) and the aqueous solution was extracted with ethyl acetate (3×). The combined organic layers were dried over sodium sulfate, filtered, and concentrated in vacuo. The resultant oil was then purified via column chromatography ($SiO_2$, Eluting solvent: commonly an initial mixture 0:100 Ethyl Acetate: Hexanes with increasing gradient to 40:60 Ethyl Acetate: Hexanes).

Synthesis of 5, 3-(3-fluoro-4-hydroxyphenyl)-3-(4-(trifluoromethoxy)phenyl)-7-(trifluoromethyl)indolin-2-one. Synthesized by general procedure A with 2-fluorophenol. 5 was isolated in 73% yield as a white solid (0.192 mmol, 0.091 g). $^{1}$H NMR ($CD_3OD$, 500 MHz) δ: 7.55 (d, J=8.0 Hz, 1H), 7.48 (d, J=7.6 Hz, 1H), 7.31 (d, J=8.9 Hz, 2H), 7.25 (d, J=8.5 Hz, 2H), 7.23 (t, J=7.9 Hz, 1H), 6.91 (dd, J=12.3, 2.4 Hz, 1H), 6.88 (t, J=8.7 Hz, 1H), 6.83 (dd, J=8.6, 2.4 Hz, 1H). $^{13}$C NMR ($CD_3OD$, 126 MHz) δ: 180.80, 152.68 (d, J=241.4 Hz), 149.94 (q, J=1.9 Hz), 146.14 (d, J=13.0 Hz), 141.74, 139.88 (q, J=2.1 Hz), 136.30, 133.33 (d, J=5.7 Hz), 131.16, 131.09, 126.18 (q, J=4.5 Hz), 125.45 (d, J=3.3 Hz), 125.1 (q, J=268.9 Hz), 124.02, 122.14, 121.79 (q, J=252.4 Hz), 118.81 (d, J=3.3 Hz), 117.17 (d, J=20.5 Hz), 113.91 (q, J=33.3 Hz), 61.92. $^{19}$F NMR ($CD_3OD$, 471 MHz) δ: −59.48, −63.01, −137.93 (dd, J=12.4, 8.9 Hz). HRMS (ESI): m/z calc. for $C_{22}H_{13}NO_3F_7$[M+H]$^+$ 472.0784, found: 472.0792. HPLC Chiral Purity (X: 254 nm): >99%. Melting Point: 92.0-95.2° C.

Synthesis of 6, 3-(3,5-difluoro-4-hydroxyphenyl)-3-(4-(trifluoromethoxy)phenyl)-7-(trifluoromethyl)indolin-2-one. Synthesized by general procedure A with 2,6-difluorophenol. 6 was isolated in 91% yield as a white solid (0.961 mmol, 0.4702 g). $^{1}$H NMR ($CD_3OD$, 500 MHz) δ: 7.57 (d, J=8.1 Hz, 1H), 7.51 (d, J=7.6 Hz, 1H), 7.37-7.18 (m, 5H), 6.83-6.70 (m, 2H). $^{13}$C NMR ($CD_3OD$, 126 MHz) δ: 180.24, 153.76 (dd, J=242.9, 7.3 Hz), 150.05 (q, J=1.6 Hz), 141.26, 139.91 (q, J=2.1 Hz), 135.65, 135.32 (t, J=16.1 Hz), 132.26 (t, J=7.7 Hz), 131.11, 131.09, 126.65 (q, J=4.5 Hz), 125.05 (q, J=271.1 Hz), 123.80, 121.86 (q, J=256.0 Hz), 122.25, 114.04 (q, J=33.3 Hz), 112.83 (m), 61.66. $^{19}$F NMR ($CD_3OD$, 471 MHz) δ: −60.23 (s), −63.80 (s), −135.17 (d, J=8.7 Hz). HRMS (ESI): m/z calc. for $C_{22}H_{12}NO_3F_8$ [M+H]$^+$ 490.0689, found: 490.0687. HPLC Chiral Purity (λ: 254 nm): 99%. Melting Point: 63.2-65.9° C.

Synthesis of 7, 3-(2-fluoro-4-hydroxyphenyl)-3-(4-(trifluoromethoxy)phenyl)-7-(trifluoromethyl)indolin-2-one. Synthesized by general procedure A with 3-fluorophenol. 6 was isolated in 68% yield as a white solid (0.359 mmol, 0.169 g). $^{1}$H NMR ($CD_3OD$, 500 MHz) δ: 7.56 (d, J=7.6 Hz, 1H), 7.44-7.32 (m, 3H), 7.31-7.13 (m, 3H), 6.84 (t, J=8.9 Hz, 1H), 6.57 (dd, J=8.7, 2.7 Hz, 1H), 6.49 (dd, J=13.0, 2.5 Hz, 1H). $^{13}$C NMR ($CD_3OD$, 126 MHz) δ: 180.91, 162.64 (d, J=246.6 Hz), 160.49 (d, J=11.98 Hz), 148.85, 140.30 (q, J=1.95 Hz), 138.98, 135.68, 131.80 (d, J=5.33 Hz), 131.12, 130.79 (d, J=2.93 Hz), 126.36 (q, J=4.43 Hz), 125.16 (q, J=271.0 Hz), 123.51, 121.92, 121.89 (q, J=255.9 Hz), 120.54 (d, J=13.41 Hz), 113.68 (q, J=33.39 Hz), 112.30 (d, J=2.69 Hz), 104.55 (d, J=24.77 Hz), 59.14. $^{19}$F NMR ($CD_3OD$, 471 MHz) δ: −60.21 (s), −63.74 (s), −110.66 (m). HRMS (ESI): m/z calc. for $C_{22}H_{13}NO_3F_7$[M+H]$^+$ 472.0784, found: 472.0779. HPLC Chiral Purity (λ: 254 nm): 97%. Melting Point: 102.5-103.9° C.

Synthesis of 8, 3-(2,6-difluoro-4-hydroxyphenyl)-3-(4-(trifluoromethoxy)phenyl)-7-(trifluoromethyl)indolin-2-one. Synthesized by general procedure A with 3,5-difluorophenol. 8 was isolated in 58% yield as a white solid (0.160 mmol, 0.078 g). $^{1}$H NMR ($CD_3OD$, 500 MHz) δ: 7.59 (d, J=8.0 Hz, 1H), 7.47 (d, J=7.5 Hz, 1H), 7.29 (d, J=8.5 Hz, 2H), 7.25 (t, J=7.8 Hz, 1H), 7.19 (d, J=8.5 Hz, 2H), 6.39 (d, J=11.8 Hz, 2H). $^{13}$C NMR ($CD_3OD$, 126 MHz) δ: 179.84, 163.02 (dd, J=247.0, 10.8 Hz), 160.85 (t, J=15.5 Hz), 150.03 (q, J=2.0 Hz), 140.39 (q, J=2.0 Hz), 140.14, 134.68, 130.56, 129.71, 126.81 (q, J=4.4 Hz), 125.08 (q, J=271.0 Hz), 123.82, 121.89 (q, J=255.7 Hz), 121.84, 113.81 (q, J=33.3 Hz), 109.16 (t, J=16.0 Hz), 101.16 (dd, J=28.01, 2.1 Hz), 56.49. $^{19}$F NMR ($CD_3OD$, 471 MHz) δ: −59.51, −63.08, −106.44 (d, 11.9 Hz). HRMS (ESI): m/z calc. for $C_{22}H_{12}NO_3F_8$ [M+H]$^+$ 490.0689, found: 490.0691. LCMS Purity (λ: 254 nm): >96%. Melting Point: >225° C.

Synthesis of 9, 3,3-bis(4-(trifluoromethoxy)phenyl)-7-(trifluoromethyl)indolin-2-one. Synthesized by general procedure A with Trifluoromethoxy-Benzene. 9 was isolated in 54% yield as a white solid (0.144 mmol, 0.075 g). $^{1}$H NMR ($CD_3OD$, 500 MHz) δ: 7.58 (d, J=7.9 Hz, 1H), 7.52 (d, J=7.3 Hz, 1H), 7.33 (d, J=9.0 Hz, 4H), 7.27 (d, J=9.0 Hz, 4H), 7.24 (t, J=7.9 Hz, 1H). $^{13}$C NMR ($CD_3OD$, 126 MHz) δ: 180.34, 150.06 (q, J=1.9 Hz), 141.38, 139.99 (q, J=1.9 Hz), 135.85, 131.23, 131.17, 126.62 (q, J=4.4 Hz), 125.07 (q, J=271.3 Hz), 123.84, 122.27, 121.87 (q, J=255.6 Hz), 114.05 (q, J=34.0 Hz), 62.30. $^{19}$F NMR ($CD_3OD$, 471 MHz) δ: −59.50, −63.05. HRMS (ESI): m/z calc. for $C_{23}H_{13}NO_3F_9$[M+H]$^+$ 522.0752, found: 522.0757. HPLC Chiral Purity (λ: 254 nm): >98%. Melting Point: 176.6-178.1° C.

Synthesis of 10, 3-(3,4-dihydroxyphenyl)-3-(4-(trifluoromethoxy) phenyl)-7-(trifluoromethyl)indolin-2-one. Synthesized by general procedure A with catechol (1,2-dihydroxybenzene). 10 was isolated in 36% yield as a white solid (0.160 mmol, 0.075 g). $^{1}$H NMR ($CD_3OD$, 500 MHz) δ: 7.53 (d, J=7.8 Hz, 1H), 7.44 (d, J=7.3 Hz, 1H), 7.34 (d, J=8.9 Hz, 2H), 7.26-7.18 (m, 3H), 6.71 (d, J=8.3 Hz, 1H), 6.67 (d, J=2.3 Hz, 1H), 6.49 (dd, J=8.3, 2.3 Hz, 1H). $^{13}$C NMR ($CD_3OD$, 126 MHz) δ: 181.34, 149.79 (q, J=1.7 Hz), 146.54, 146.31, 142.05, 139.85 (q, J=2.0 Hz), 136.99, 133.33, 131.29, 131.06, 126.07 (q, J=4.5 Hz), 125.16 (q, J=270.8 Hz), 123.49, 121.97, 121.89 (q, J=255.8 Hz), 120.66, 116.68, 116.25, 113.72 (q, J=31.5 Hz), 62.29. $^{19}$F NMR ($CD_3OD$, 471 MHz) δ: −59.49, −62.98. HRMS (ESI):

m/z calc. for $C_{22}H_{14}NO_4F_6$ $[M+H]^+$ 470.0827, found: 470.0828. HPLC Chiral Purity (λ: 254 nm): >98%. Melting Point: 95.8-101.9° C.

Separation of (S)-10, (S)-3-(3,4-dihydroxyphenyl)-3-(4-(trifluoromethoxy)phenyl)-7-(trifluoromethyl)indolin-2-one. 10 was separated into its respective enantiomers using preparative chiral HPLC separation (Lux® 5 uM Cellulose-1, 250×21.2 mm, AXIA™ Packed, isocratic: 40% i-PrOH/Hexanes). (S)-10 was isolated as a white solid. $^1$H NMR ($CD_3OD$, 500 MHz) δ: 7.53 (d, J=8.0 Hz, 1H), 7.44 (d, J=7.5 Hz, 1H), 7.34 (d, J=8.9 Hz, 2H), 7.29-7.16 (m, 3H), 6.71 (d, J=8.3 Hz, 1H), 6.66 (d, J=2.3 Hz, 1H), 6.49 (dd, J=8.4, 2.3 Hz, 1H). $^{13}$C NMR ($CD_3OD$, 126 MHz) δ: 181.36, 149.80 (q, J=1.7 Hz), 146.56, 146.33, 142.06, 139.85 (q, J=2.1 Hz), 136.99, 133.34, 131.30, 131.07, 126.07 (q, J=4.6 Hz), 125.17 (q, J=270.8 Hz), 123.49, 121.97, 121.89 (q, J=255.8 Hz), 120.66, 116.68, 116.26, 113.73 (q, J=31.5 Hz), 62.29. $^{19}$F NMR ($CD_3OD$, 471 MHz) δ: −59.49, −62.97. HRMS (ESI): m/z calc. for $C_{22}H_{14}NO_4F_6$ $[M+H]^+$ 470.0827, found: 470.0829. HPLC Chiral Purity (λ: 254 nm): >98%. Melting Point: 223.7-225.0° C.

Synthesis of 11, 3-(4-hydroxy-3-methylphenyl)-3-(4-(trifluoromethoxy)phenyl)-7-(trifluoromethyl)indolin-2-one. Synthesized by general procedure A with 2-methylphenol. 11 was isolated in 83% yield as a white solid (0.436 mmol, 0.2035 g). $^1$H NMR ($CD_3OD$, 500 MHz) δ: 7.53 (d, J=7.7 Hz, 1H), 7.44 (d, J=7.3 Hz, 1H), 7.31 (d, J=8.9 Hz, 2H), 7.25-7.16 (m, 3H), 6.92 (dd, J=2.5, 0.8 Hz, 1H), 6.82 (dd, J=8.4, 2.5 Hz, 1H), 6.69 (d, J=8.4 Hz, 1H), 2.11 (s, 3H). $^{13}$C NMR ($CD_3OD$, 126 MHz) δ: 180.21, 157.12, 149.80 (q, J=1.8 Hz), 142.22, 139.81 (q, J=2.1 Hz), 137.05, 132.51, 131.61, 131.24, 131.07, 127.68, 126.07 (m, complex, ~2 carbons), 125.16 (q, J=271.0 Hz), 123.52, 121.96, 121.89 (q, J=255.7 Hz), 115.57, 113.74 (q, J=33.3 Hz), 63.08, 16.33. $^{19}$F NMR ($CD_3OD$, 471 MHz) δ: −60.21 (s), −63.69 (s). HRMS (ESI): m/z calc. for $C_{23}H_{16}NO_3F_6$ $[M+H]^+$ 468.1034, found: 468.1032. HPLC Chiral Purity (λ: 254 nm): 99%. Melting Point: 93.3-98.2° C.

Synthesis of 12, 3-(4-hydroxy-3,5-dimethylphenyl)-3-(4-(trifluoromethoxy)phenyl)-7-(trifluoromethyl)indolin-2-one. Synthesized by general procedure A with 2,6-dimethylphenol. 12 was isolated in 76% yield as an off-white solid (0.203 mmol, 0.098 g). $^1$H NMR ($CD_3OD$, 500 MHz) δ: 7.53 (d, J=8.0 Hz, 1H), 7.45 (q, J=1.9 Hz, 1H), 7.30 (d, J=8.9 Hz, 2H), 7.22 (d, J=8.4 Hz, 2H), 7.20 (t, J=7.7 Hz, 1H), 6.76 (s, 2H), 2.17 (s, 6H). $^{13}$C NMR ($CD_3OD$, 126 MHz) δ: 181.52, 154.21, 149.79, 142.18, 139.79 (q, J=1.88 Hz), 137.09, 132.76, 131.27, 131.08, 129.20, 126.04 (q, J=4.43 Hz), 125.93, 125.18 (q, J=270.0 Hz), 123.51, 121.94, 121.89 (q, J=255.4 Hz), 113.72 (q, J=32.95 Hz), 62.30, 16.78. $^{19}$F NMR ($CD_3OD$, 471 MHz) δ: −59.47, −62.95. HRMS (ESI): m/z calc. for $C_{24}H_{18}NO_3F_6$ $[M+H]^+$ 482.1191, found: 482.1195. HPLC Chiral Purity (λ: 254 nm): >98%. Melting Point: 177.2-189.4° C.

Synthesis of 13, 3-(4-hydroxy-3,5-diisopropylphenyl)-3-(4-(trifluoromethoxy)phenyl)-7-(trifluoromethyl)indolin-2-one. Synthesized by general procedure A with 2,6-diisopropylphenol. 13 was isolated in 64% yield as an off-white solid (0.169 mmol, 0.091 g). $^1$H NMR ($CD_3OD$, 500 MHz) δ: 7.54 (d, J=7.8 Hz, 1H), 7.42 (d, J=7.3 Hz, 1H), 7.29 (d, J=9.0 Hz, 2H), 7.23 (d, J=9.0 Hz, 2H), 7.22 (t, J=7.7 Hz, 1H), 6.86 (s, 2H) 3.26 (septet, J=6.9 Hz, 2H), 1.10 (dd, J=6.7, 1.5 Hz, 12H). $^{13}$C NMR ($CD_3OD$, 126 MHz) δ: 181.60, 151.72, 149.78 (q, J=1.5 Hz), 142.34, 139.88 (q, J=2.1 Hz), 137.26, 136.99, 133.02, 131.27, 130.99, 126.04 (q, J=4.4 Hz), 125.19 (q, J=268.9 Hz), 124.34, 123.43, 121.90, 121.88 (q, J=256.5 Hz), 113.85 (q, J=32.9 Hz), 62.73, 23.30, 23.25. $^{19}$F NMR ($CD_3OD$, 471 MHz) δ: −59.50, −62.96. HRMS (ESI): m/z calc. for $C_{28}H_{26}NO_3F_6$ $[M+H]^+$ 538.1817, found: 538.1819. HPLC Chiral Purity (λ: 254 nm): 97%. Melting Point: 77.5-79.0° C.

Synthesis of 14, 3-(4-((tert-butyldimethylsilyl)oxy)phenyl)-3-hydroxy-7-(trifluoromethyl) indolin-2-one. A flame-dried round bottom flask under inert atmosphere was charged with (4-bromophenoxy)(tert-butyl)dimethylsilane (29.30 mmol, 7.2 mL) and dissolved in THF (31 mL). The reaction mixture was cooled to −78° C. and a solution of n-BuLi (27.90 mmol, 18.6 mL) added dropwise over 10 minutes. The reaction was stirred for 1 hour at −78° C. In another flame-dried flask, 7-(trifluoromethyl)indoline-2,3-dione (13.95 mmol, 3.0 g) was added and dissolved in THF (31 mL) under inert atmosphere. This solution of isatin at room temperature was added to the reaction vessel at −78° C. dropwise over 15 minutes. The resultant mixture was stirred at −78° C. for 1 hour, removed from the cold bath, allowed warmed to room temperature while stirring for 30 minutes. The reaction was quenched with water (20 mL). The solution was poured into a separatory funnel with 100 mL EtOAc and 100 mL of 1:1 $H_2O$:Saturated Brine. The organics were extracted with ethyl acetate (3×, ~50-100 mL) and the combined organic layers washed with brine, then dried over sodium sulfate, filtered, and concentrated in vacuo. The resultant oil was purified via automated flash chromatography ($SiO_2$, eluting solvent: initial mixture 0:100 Ethyl Acetate:Hexanes with increasing gradient to 40:60 Ethyl Acetate:Hexanes over 20 column volumes). 14 was isolated in 79% yield as a yellow solid (11.04 mmol, 4.67 g). $^1$H NMR ($CD_3OD$, 500 MHz) δ: 7.54 (d, J=7.8 Hz, 1H), 7.43 (d, J=7.2 Hz, 1H), 7.26 (d, J=8.7 Hz, 2H), 7.18 (dd, J=8.1, 7.4 Hz, 1H), 6.81 (d, J=8.7 Hz, 2H), 0.97 (s, 9H), 0.18 (s, 6H). $^{13}$C NMR ($CD_3OD$, 126 MHz) δ: 181.43, 157.02, 140.53 (q, J=2.3 Hz), 136.68, 134.05, 129.89, 128.11, 126.98 (q, J=4.5 Hz), 125.12 (q, J=271.0), 123.80, 121.01, 113.60 (q, J=33.2 Hz), 77.63, 26.12, 19.03, −4.34. $^{19}$F NMR ($CD_3OD$, 471 MHz) δ: −62.86 (s). HRMS (ESI): m/z calc. for $C_{21}H_{25}F_3NO_3Si$ $[M+H]^+$ 424.1556, found: 424.1563. Melting Point: 71.9-73.9° C.

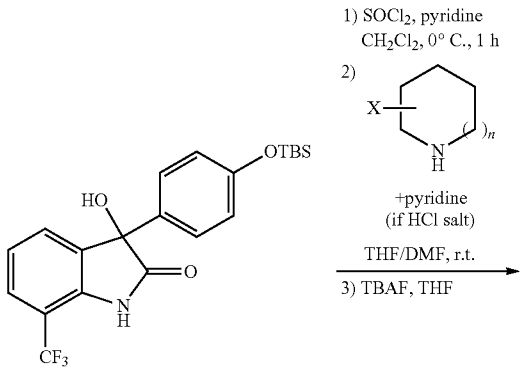

14

-continued

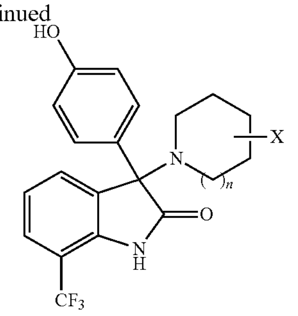

2, 16-21
41-83%
over 3 steps

General Procedure B (Compounds 2, 16-21). A round bottom flask charged with compound 14 (0.394 mmol) dissolved in dichloromethane (2.9 mL) was cooled to 0° C. Pyridine (0.8 mmol, 0.06 mL) then thionyl chloride ($SOCl_2$, 0.591 mmol, 0.04 mL) were added and the reaction stirred for 1 hour. Water (~5 mL) was then added with vigorous stirring. The biphasic mixture was then extracted with ethyl acetate (3 times) and the combined organic layers washed with brine, dried over sodium sulfate, and concentrated in vacuo. A clean reaction vessel was charged with the crude mixture and dissolved in THF or DMF (3.9 mL) followed by the desired amine (3.94 mmol), and pyridine (3.94 mmol) if the desired amine is an HCl salt. The reaction mixture was stirred for 2-4 hours (reaction tracked by TLC to monitor the consumption of starting material). The reaction was poured into a 1:1 water:brine and extracted with ethyl acetate (3 times) and the combined organic layers dried over sodium sulfate and concentrated in vacuo. The crude oil was then dissolved in THF (4 mL) and a TBAF solution (1M in THF, 2 mL) was added and the reaction stirred until complete consumption of starting material was observed (reaction monitored by TLC). Upon completion, the mixture was poured into 1:1 saturated sodium bicarbonate:brine and extracted with ethyl acetate (3 times) with the resultant combined organic layers dried over sodium sulfate and concentrated in vacuo. Final compounds were purified via automated flash chromo column chromatography ($SiO_2$, loaded onto columns with $CH_2Cl_2$ or diethyl ether, eluting solvent: initial mixture 0:100 Ethyl Acetate:Hexanes with increasing gradient to 100:0 Ethyl Acetate:Hexanes over ~20-30 column volumes). Note: Scheme 3B, general procedure C below) is the ideal synthetic route for synthesizing compounds of this type.

Synthesis of 2, 3-(4,4-difluoropiperidin-1-yl)-3-(4-hydroxyphenyl)-7-(trifluoromethyl)indolin-2-one. Synthesized by general procedure B with 4,4-difluoropiperdine hydrochloride. 2 was isolated in 54% yield as a white solid (0.213 mmol, 0.0875 g) and 83% yield as a white solid (2.45 mmol, 1.01 g). We have observed batch to batch variability with this reaction.

$^1H$ NMR ($CD_3OD$, 500 MHz) δ: 7.56 (d, J=7.5 Hz, 1H), 7.52 (d, J=8.0 Hz, 1H), 7.33 (d, J=8.5 Hz, 2H), 7.20 (t, J=7.8 Hz, 1H), 6.77 (d, J=8.4 Hz, 2H), 2.95-2.45 (m, 4H), 2.02-1.87 (m, 4H). $^{13}C$ NMR ($CD_3OD$, 126 MHz) δ: 179.94, 158.93, 140.07 (q, J=2.2 Hz), 133.36, 130.46, 130.03, 129.45, 126.51 (q, J=4.5 Hz), 125.12 (q, J=271.0 Hz), 123.37, 123.0 (t, J=241.0 Hz), 116.58, 113.63 (q, J=33.1 Hz), 74.00, 45.13 (t, J=5.5 Hz), 35.70 (t, J=22.9 Hz). $^{19}F$ NMR ($CD_3OD$, 471 MHz) δ: −63.70, −99.68 (bs). HRMS (ESI): m/z calc. for $C_{20}H_{18}N_2O_2F_5$ $[M+H]^+$ 413.1288, found: 413.1288. HPLC Chiral Purity (λ: 254 nm): >99% (racemic). Melting Point: 93.5-95.2° C.

Synthesis of 16, 3-(4-hydroxyphenyl)-3-(piperidin-1-yl)-7-(trifluoromethyl)indolin-2-one. Synthesized by general procedure B with piperdine. 16 was isolated in 65% yield as a white solid (0.257 mmol, 0.0966 g). $^1H$ NMR ($CD_3OD$, 500 MHz) δ: 7.60-7.43 (m, 2H), 7.30 (d, J=8.4 Hz, 2H), 7.19 (t, J=7.8 Hz, 1H), 6.74 (d, J=8.7 Hz, 2H), 2.60-2.39 (m, 4H), 1.66-1.49 (m, 4H), 1.49-1.36 (m, 2H). $^{13}C$ NMR ($CD_3OD$, 126 MHz) δ: 180.49, 158.62, 140.22 (q, J=2.3 Hz), 133.68, 130.72, 130.40, 129.71, 126.17 (q, J=4.4 Hz), 125.21 (q, J=271.2 Hz), 123.04, 116.33, 113.38 (q, J=33.1 Hz), 74.94, 40.42, 27.64, 25.84. $^{19}F$ NMR ($CD_3OD$, 471 MHz) δ: −63.66. HRMS (ESI): m/z calc. for $C_{20}H_{20}F_3N_2O_2$ $[M+H]^+$ 377.1477, found: 377.1491. HPLC Chiral Purity (λ: 254 nm): >99%. Melting Point: 99.6-100.7° C.

Synthesis of 17, 3-(4,4-difluoro-3-methylpiperidin-1-yl)-3-(4-hydroxyphenyl)-7-(trifluoromethyl)indolin-2-one. Synthesized by general procedure B with 4,4-difluoro-3-methylpiperidine hydrochloride. 17 (racemic mixture of diastereomers, 4 total compounds) was isolated in 71% yield as a white solid (1.38 mmol, 0.586 g). $^1H$ NMR ($CD_3OD$, 500 MHz) δ: 7.63-7.45 (m, 2H), 7.33 (d, J=8.2 Hz, 2H), 7.23-7.11 (m, 1H), 6.77 (d, J=8.4 Hz, 2H), 2.84-2.60 (m, 2H), 2.60-2.48 (m, 1H), 2.28 (q, J=11.4 Hz, 1H), 2.19-1.75 (m, 3H), 1.06-0.77 (m, 3H). $^{13}C$ NMR ($CD_3OD$, 126 MHz) δ: 179.95/179.90 (2 signals-diastereomers), 158.93, 140.06 (m), 133.35/133.30 (2 signals-diastereomers), 130.48, 130.05/130.02 (2 signals-diastereomers), 129.52/129.48 (2 signals-diastereomers), 126.51 (q, J=4.6 Hz), 125.12 (q, J=270.9 Hz), 123.94/123.90 (2 signals-diastereomers, t, J~247.0 Hz), 123.35, 116.57, 113.62 (q, J=33.5 Hz), 73.86, 51.95 (t, J=9.3 Hz), 45.37 (m), 39.77 (m), 34.98 (t, J=23.5 Hz), 10.51 (m). $^{19}F$ NMR ($CD_3OD$, 471 MHz) δ: −63.68, −102.29 (m). HRMS (ESI): m/z calc. for $C_{21}H_{20}F_5N_2O_2$ $[M+H]^+$ 427.1445, found: 427.1426. HPLC Chiral Purity (λ: 254 nm): 99%. Melting Point: 109.5-114.5° C. (decomposition).

Synthesis of 18, 3-(4-hydroxyphenyl)-3-morpholino-7-(trifluoromethyl)indolin-2-one. Synthesized by general procedure B with morpholine. 18 was isolated in 70% yield as a white solid (0.277 mmol, 0.1046 g). $^1H$ NMR ($CD_3OD$, 500 MHz) δ: 7.56 (d, J=7.5 Hz, 1H), 7.51 (d, J=8.1 Hz, 1H), 7.35 (d, J=8.2 Hz, 2H), 7.20 (dd, J=8.1, 7.5 Hz, 1H), 6.76 (d, J=8.4 Hz, 2H), 3.70-3.58 (m, 4H), 2.62-2.50 (m, 4H). $^{13}C$ NMR ($CD_3OD$, 126 MHz) δ: 179.78, 158.82, 140.24 (q, J=2.43 Hz), 133.15, 130.72, 129.90, 129.38, 126.45 (q, J=4.47 Hz), 125.10 (q, J=270.92 Hz), 123.26, 116.51, 113.52 (q, J=33.18 Hz), 74.20, 68.51, 48.75. $^{19}F$ NMR ($CD_3OD$, 471 MHz) δ: −63.67 (s). HRMS (ESI): m/z calc. for $C_{19}H_{18}F_3N_2O_3$ $[M+H]^+$ 379.1270, found: 379.1273. HPLC Chiral Purity (λ: 254 nm): 99%. Melting Point: 214.7-215.0° C. (decomposition).

Synthesis of 19, 3-(azepan-1-yl)-3-(4-hydroxyphenyl)-7-(trifluoromethyl)indolin-2-one. Synthesized by general procedure B with azepane. 19 was isolated in 56% yield as an off-white solid (0.133 mmol, 0.052 g). $^1H$ NMR ($CD_3OD$, 500 MHz) δ: 7.57 (d, J=7.5 Hz, 1H), 7.48 (d, J=8.1 Hz, 1H), 7.33 (d, J=8.8 Hz, 2H), 7.18 (t, J=7.8 Hz, 1H), 6.73 (d, J=8.8 Hz, 2H), 2.76-2.45 (m, 4H), 1.79-1.49 (m, 8H). $^{13}C$ NMR ($CD_3OD$, 126 MHz) δ: 181.24, 158.66, 139.92 (q, J=2.1 Hz), 134.97, 131.95, 130.18, 129.65, 126.08 (q, J=4.5 Hz), 125.21 (q, J=270.7 Hz), 123.19, 116.28, 113.40 (q, J=33.2 Hz), 75.76, 52.23, 31.03, 27.53. $^{19}F$ NMR ($CD_3OD$, 471 MHz) δ: −63.68. HRMS (ESI): m/z calc. for $C_{21}H_{22}F_3N_2O_2$ $[M+H]^+$ 391.1633, found: 391.1619. HPLC Chiral Purity (λ: 254 nm): 98%. Melting Point: 103.1-104.3° C.

Synthesis of 20, 3-(4-hydroxyphenyl)-3-(4-hydroxypiperidin-1-yl)-7-(trifluoromethyl)indolin-2-one. Synthesized by general procedure B with piperidin-4-ol. 20 was isolated in 67% yield as an off-white solid (0.135 mmol, 0.053 g). $^1$H NMR ($CD_3OD$, 500 MHz) δ: 7.60-7.41 (m, 2H), 7.31 (d, J=8.3 Hz, 2H), 7.19 (t, J=7.8 Hz, 1H), 6.75 (d, J=8.4 Hz, 2H), 3.60-3.45 (m, 1H), 2.94-2.64 (m, 2H), 2.42-2.21 (m, 2H), 1.85-1.74 (m, 2H), 1.62-1.44 (m, 2H). $^{13}$C NMR ($CD_3OD$, 126 MHz) δ: 180.33, 158.72, 140.14 (q, J=1.5 Hz), 133.64, 130.64, 130.39, 129.58, 126.26 (q, J=4.6 Hz) 125.19 (q, J=271.3 Hz) 123.16, 116.41, 113.44 (q, J=33.2 Hz), 74.40, 68.91, 46.05, 35.85. $^{19}$F NMR ($CD_3OD$, 471 MHz) δ: −63.67. HRMS (ESI): m/z calc. for $C_{20}H_{20}F_3N_2O_3$ $[M+H]^+$ 393.1426, found: 393.1424. HPLC Chiral Purity (λ: 254 nm): 99%. Melting Point: 143.5° C. (decomposition).

Synthesis of 21, 3-(4-hydroxyphenyl)-3-(4-(trifluoromethoxy)piperidin-1-yl)-7-(trifluoromethyl)indolin-2-one. Synthesized by general procedure B with 4-(trifluoromethoxy)piperidine. 21 was isolated in 41% yield as an off-white solid (0.096 mmol, 0.0443 g). $^1$H NMR ($CD_3OD$, 500 MHz) δ: 7.55 (d, J=7.5 Hz, 1H), 7.51 (d, J=8.0 Hz, 1H), 7.32 (d, J=8.4 Hz, 2H), 7.20 (t, J=7.8 Hz, 1H), 6.76 (d, J=8.8 Hz, 2H), 4.39-4.24 (m, 1H), 2.87-2.64 (m, 2H), 2.54-2.22 (m, 2H), 2.09-1.90 (m, 2H), 1.85-1.69 (m, 2H). $^{13}$C NMR ($CD_3OD$, 126 MHz) δ: 180.10, 158.83, 140.12 (q, J=2.6 Hz), 133.46, 130.56, 130.12, 129.54, 126.41 (q, J=4.5 Hz), 126.23 (q, J=270.9 Hz), 123.30, 123.09 (q, J=252.6 Hz), 116.50, 113.55 (q, J=33.2 Hz), 76.84 (m), 74.28, 45.21, 33.37. $^{19}$F NMR ($CD_3OD$, 471 MHz) δ: −59.98, −63.69. HRMS (ESI): m/z calc. for $C_{21}H_{19}F_6N_2O_3$ $[M+H]^+$ 461.1300, found: 461.1300. HPLC Chiral Purity (λ: 254 nm): 99%. Melting Point: 100.4-101.8° C.

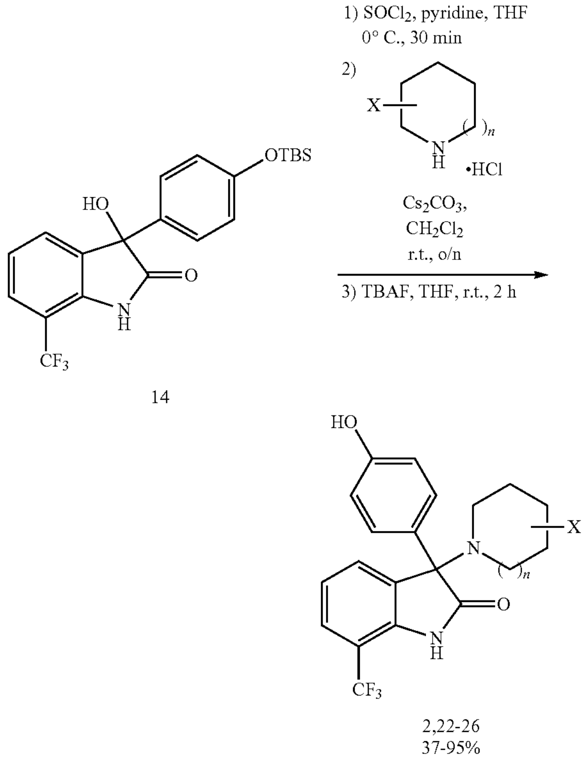

14

2,22-26
37-95%
over three steps

General Procedure C (Compounds 2, 22-26). To a flame-dried flask charged with 14 (1.77 mmol, 0.75 g), THF (5.9 mL) was added and cooled to 0° C. Pyridine (5.32 mmol, 0.42 mL) then thionyl chloride ($SOCl_2$, 8.85 mmol, 0.65 mL) were added until starting material (14) was consumed as monitored by TLC (40:60 ethyl acetate:hexanes); approximately 30 minutes after $SOCl_2$ addition. ~30 mL of water was then added to the reaction with vigorous stirring. The resultant solution was then extracted with ethyl acetate (3×) and the combined organic layers wash with brine, dried over sodium sulfate, filtered, and concentrated in vacuo. The crude oil was dissolved in $CH_2Cl_2$ (25.5 mL) and desired amine hydrochloride salt (3.55 mmol, 0.56 g) was added, followed by cesium carbonate ($Cs_2CO_3$, 14.18 mmol, 5.01 g). The reaction stirred overnight (~16-18 hours) and then poured into water (~100 mL). Organics were extracted with $CH_2Cl_2$ (3×), and the combined organic layers were washed with 1:1 Brine:saturated Sodium Bicarbonate, dried over sodium sulfate, filtered, and concentrated in vacuo. The resulting crude yellow oil was then dissolved in THF (9.3 mL) followed by the addition of TBAF in THF solution (1 M, 7.2 mL). The reaction turned a pale green upon the addition of TBAF and the reaction stirred for 2 hours. The reaction mixture was poured into saturated Sodium Bicarbonate (~50 mL) and extracted with ethyl acetate (3×), washed with 1:1 Brine:saturated Sodium Bicarbonate, dried over sodium sulfate, filtered, and concentrated in vacuo. Crude product was purified via column chromatography ($SiO_2$, Typical Column conditions: Eluting solvent: an initial mixture 0:100 Ethyl Acetate:Hexanes for 2 column volumes then an increasing gradient to 35:65 Ethyl Acetate:Hexanes for 10 column volumes, followed by a maintained 35:65 Ethyl Acetate:Hexanes for 2 column volumes, ending finally with an increasing gradient to 70% Ethyl Acetate:Hexanes for 3.5 column volumes.

Optimized Synthesis (Scheme 3B) of 2, 3-(4,4-difluoropiperidin-1-yl)-3-(4-hydroxyphenyl)-7-(trifluoromethyl) indolin-2-one. 2 was isolated in 95% yield as an off-white solid (1.69 mmol, 0.696 g). All characterization data consistent with above reported 2 using General Procedure B.

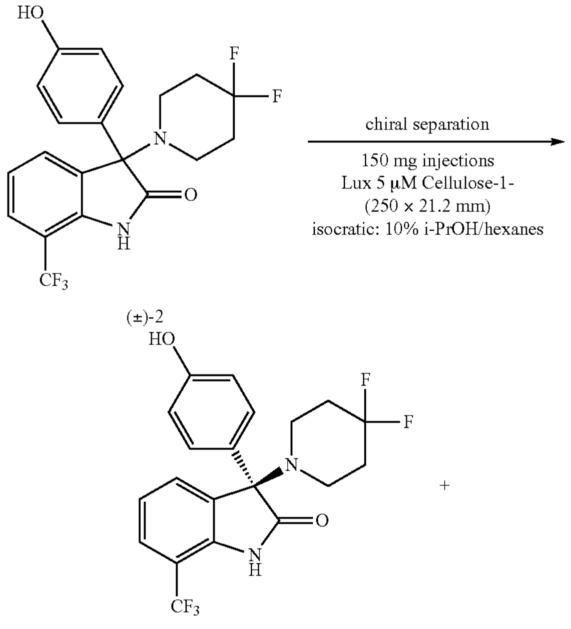

(±)-2

+

(R)-2 (ErSO-DFP)
First Peak

-continued

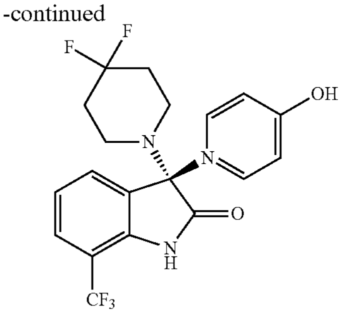

(S)-2
Second Peak

Chiral Separation and Isolation of (R)-2, ErSO-DFP, (R)-3-(4,4-difluoropiperidin-1-yl)-3-(4-hydroxyphenyl)-7-(trifluoromethyl)indolin-2-one and (S)-2, (S)-3-(4,4-difluoropiperidin-1-yl)-3-(4-hydroxyphenyl)-7-(trifluoromethyl) indolin-2-one. 2 was separated into its respective enantiomers using preparative chiral HPLC separation (Lux® 5 μM Cellulose-1, LC Column, 250×21.2 mm, AXIA™ Packed, isocratic: 10% i-PrOH/hexanes). The chiral separation yields: (R)-2 (first peak on HPLC) as a white solid after lyophilization from neat acetonitrile. $^{1}H$ NMR ($CD_3OD$, 500 MHz) δ: 7.56 (d, J=7.5 Hz, 1H), 7.52 (d, J=8.0 Hz, 1H), 7.33 (d, J=8.4 Hz, 2H), 7.24-7.14 (m, 1H), 6.77 (d, J=8.4 Hz, 2H), 2.80-2.51 (m, 4H), 2.02-1.85 (m, 4H). $^{13}C$ NMR ($CD_3OD$, 126 MHz) δ: 179.94, 158.92, 140.09 (q, J=2.2 Hz), 133.37, 130.47, 130.05, 129.46, 126.53 (q, J=4.4 Hz), 125.12 (q, J=271.1 Hz), 123.37, 123.01 (t, J=241.0 Hz), 116.58, 113.63 (q, J=33.2), 74.00, 45.13 (t, J=5.6 Hz), 35.70 (t, J=22.9 Hz). $^{19}F$ NMR ($CD_3OD$, 471 MHz) δ: −62.97 (s), −98.87 (bs). HRMS (ESI): m/z calc. for $C_{20}H_{18}F_5N_2O_2$[M+H]$^+$ 413.1288, found: 413.1279. Full structure elucidation performed by COSY, HSQC, HMBC, and DEPT135. Crystal Structure was confirmed by X-ray. HPLC Chiral Purity (λ: 254 nm): >99%. Melting Point: 214.1-215.7° C.

(S)-2 (second peak on HPLC) as a white solid after lyophilization from neat acetonitrile. $^{1}H$ NMR ($CD_3OD$, 500 MHz) δ: 7.56 (d, J=7.5 Hz, 1H), 7.52 (d, J=7.7 Hz, 1H), 7.33 (d, J=8.7 Hz, 2H), 7.24-7.15 (m, 1H), 6.77 (d, J=9.0 Hz, 2H), 2.71-2.50 (m, 4H), 2.03-1.76 (m, 4H). $^{13}C$ NMR ($CD_3OD$, 126 MHz) δ: 179.93, 158.91, 140.08 (q, J=2.3 Hz), 133.36, 130.46, 130.04, 129.45, 126.51 (q, J=4.5 Hz), 125.12 (q, J=270.9 Hz), 123.36, 123.00 (t, J=241.0 Hz), 116.57, 113.62 (q, J=33.2 Hz), 74.00, 45.13 (t, J=5.6 Hz), 35.71 (t, J=22.9 Hz). $^{19}F$ NMR ($CD_3OD$, 471 MHz) δ: −62.97 (s), −98.97 (bs). HRMS (ESI): m/z calc. for $C_{20}H_{18}F_5N_2O_2$[M+H]$^+$ 413.1288, found: 413.1277. Crystal Structure: confirmed by X-ray analysis. HPLC Chiral Purity (λ: 254 nm): >99%. Melting Point: 198.0-199.1° C.

Synthesis of (R)-22, (R)-3-(4-fluoropiperidin-1-yl)-3-(4-hydroxyphenyl)-7-(trifluoromethyl)indolin-2-one. Synthesized by general procedure C with 4-fluoropiperidine hydrochloride. 22 was isolated in 57% yield as an off-white solid (0.538 mmol, 0.212 g). (R)-22 was isolated using preparative chiral HPLC separation (Lux® 5 μM Cellulose-1, LC Column, 250×21.2 mm, AXIA™ Packed, isocratic: 10% i-PrOH/hexanes). $^{1}H$ NMR ($CD_3OD$, 500 MHz) δ: 7.76-7.43 (m, 2H), 7.32 (d, J=8.6 Hz, 2H), 7.19 (t, J=7.8 Hz, 1H), 6.75 (d, J=9.0 Hz, 2H), 4.59 (dtt, J=48.6, 6.9, 3.5 Hz, 1H), 2.80-2.59 (m, 2H), 2.52-2.40 (m, 2H), 2.00-1.63 (m, 4H). $^{13}C$ NMR ($CD_3OD$, 126 MHz) δ: 180.22, 158.77, 140.16 (q, J=2.2 Hz), 133.49, 130.62, 130.22, 129.57, 126.35 (q, J=4.6 Hz), 125.16 (q, J=271.0 Hz), 123.22, 116.45, 113.50 (q, J=33.2 Hz), 89.59 (d, J=170.5 Hz), 74.43, 44.56 (dd, J=17.4, 6.5 Hz), 33.25 (dd, J=19.5, 6.9 Hz). $^{19}F$ NMR ($CD_3OD$, 471 MHz) δ: −63.68, −182.68 (bs). HRMS (ESI): m/z calc. for $C_{20}H_{19}F_4N_2O_2$[M+H]$^+$ 395.1383, found: 395.1368. HPLC Chiral Purity (λ: 254 nm): >99%. Melting Point: 100.9° C. (decomposition).

Synthesis of (R)-23, (R)-3-(3,3-difluoropiperidin-1-yl)-3-(4-hydroxyphenyl)-7-(trifluoromethyl)indolin-2-one. Synthesized by general procedure C with 3,3-difluoropiperidine hydrochloride. 23 was isolated in 58% yield as an off-white solid (0.206 mmol, 0.085 g). (R)-23 was isolated using preparative chiral HPLC separation (Lux® 5 μM Cellulose-1, LC Column, 250×21.2 mm, AXIA™ Packed, isocratic: 10% i-PrOH/hexanes). $^{1}H$ NMR ($CD_3OD$, 500 MHz) δ: 7.55-7.45 (m, 2H), 7.35 (d, J=8.7 Hz, 2H), 7.18 (t, J=7.8 Hz, 1H), 6.78 (d, J=8.8 Hz, 2H), 2.87-2.74 (m, 2H), 2.56-2.40 (m, 2H), 1.98-1.79 (m, 2H), 1.77-1.62 (m, 2H). $^{13}C$ NMR ($CD_3OD$, 126 MHz) δ: 179.60, 158.89, 139.99 (q, J=2.4 Hz), 133.66, 130.29, 129.72, 129.56, 126.50 (q, J=4.6 Hz), 125.10 (q, J=271.0 Hz), 123.48, 121.53 (t, 241.0 Hz), 116.60, 113.61 (q, J=33.3 Hz), 73.66, 53.91 (t, J=29.2 Hz), 47.71, 33.60 (t, J=23.3 Hz), 23.43 (t, J=23.4 Hz). $^{19}F$ NMR ($CD_3OD$, 471 MHz) δ: −63.71, −102.32 (m). HRMS (ESI): m/z calc. for $C_{20}H_{16}F_5N_2O_2$[M−H]$^-$ 411.1132, found: 411.1119. HPLC Chiral Purity (λ: 254 nm): >99%. Melting Point: 96.3-100.3° C. (decomposition).

Synthesis of (R)-24, (R)-3-(3,3-difluoropyrrolidin-1-yl)-3-(4-hydroxyphenyl)-7-(trifluoromethyl)indolin-2-one. Synthesized by general procedure C with 3,3-difluoropyrrolidine hydrochloride. 24 was isolated in 66% yield as a white solid (0.231 mmol, 0.092 g). (R)-24 was isolated using preparative chiral HPLC separation (Lux® 5 μM Cellulose-1, LC Column, 250×21.2 mm, AXIA™ Packed, isocratic: 10% i-PrOH/hexanes). $^{1}H$ NMR ($CD_3OD$, 500 MHz) δ: 7.56 (d, J=7.5 Hz, 1H), 7.51 (d, J=8.1 Hz, 1H), 7.36 (d, J=8.9 Hz, 2H), 7.19 (t, J=7.8 Hz, 1H), 6.78 (d, J=8.8 Hz, 2H), 3.13 (ddd, J=15.1, 12.6, 10.6 Hz, 1H), 2.96 (dt, J=14.4, 11.1 Hz, 1H), 2.86 (dt, J=9.1, 6.7 Hz, 1H), 2.76 (dt, J=9.3, 7.2 Hz, 1H), 2.28-2.14 (m, 2H). $^{13}C$ NMR ($CD_3OD$, 126 MHz) δ: 179.63, 158.87, 139.78 (q, J=2.1 Hz), 133.50, 130.36 (t, J=246.9 Hz), 130.35, 129.64, 129.36, 126.62 (q, J=4.5 Hz), 125.08 (q, J=270.9 Hz), 123.51, 116.57, 113.64 (q, J=33.2 Hz), 70.90, 56.33 (t, J=30.5 Hz), 46.61 (t, J=3.6 Hz), 36.15 (t, J=24.5 Hz). $^{19}F$ NMR ($CD_3OD$, 471 MHz) δ: −63.71, −95.78 (p, J=14.2 Hz), −95.93 (qd, J=14.9, 11.25 Hz). HRMS (ESI): m/z calc. for $C_{19}H_{14}F_5N_2O_2$[M−H]$^-$ 397.0975, found: 397.0974. HPLC Chiral Purity (λ: 254 nm): >99%. Melting Point: 98.7° C. (decomposition).

Synthesis of (R)-25, (R)-3-(3,3-difluoroazetidin-1-yl)-3-(4-hydroxyphenyl)-7-(trifluoromethyl)indolin-2-one. Synthesized by general procedure C with 3,3-difluoroazetidine hydrochloride. 25 was isolated in 37% yield as a white solid (1.31 mmol, 0.502 g). (R)-25 was isolated using preparative chiral HPLC separation (Lux® 5 μM Cellulose-1, LC Column, 250×21.2 mm, AXIA™ Packed, isocratic: 10% i-PrOH/hexanes). $^{1}H$ NMR ($CD_3OD$, 500 MHz) δ: 7.49 (dd, J=11.6, 7.8 Hz, 2H), 7.35 (d, J=8.7 Hz, 2H), 7.14 (t, J=7.8 Hz, 1H), 6.78 (d, J=8.7 Hz, 2H), 3.93 (td, J=12.5, 9.6 Hz, 2H), 3.52 (td, J=12.4, 9.6 Hz, 2H). $^{13}C$ NMR ($CD_3OD$, 126 MHz) δ: 180.00, 158.91, 139.80 (q, J=2.0 Hz), 133.67, 130.09, 129.36, 129.18, 126.84 (q, J=4.5 Hz), 125.04 (q, J=270.9 Hz), 123.75, 117.43 (t, J=272.7 Hz), 116.68, 113.70 (q, J=33.3 Hz), 72.45, 60.01 (t, J=24.5 Hz). $^{19}F$ NMR ($CD_3OD$, 471 MHz) δ: −63.64, −102.64 (p, J=12.4 Hz). HRMS (ESI): m/z calc. for $C_{18}H_{12}F_5N_2O_2$[M−H]$^-$ 383.0819, found: 383.0822. HPLC Chiral Purity (λ: 254 nm): >99%. Melting Point: 79.0-83.9° C.

Synthesis of (R)-26, (R)-3-(4-hydroxyphenyl)-3-(3,3,4,4-tetrafluoropyrrolidin-1-yl)-7-(trifluoromethyl)indolin-2-one. Synthesized by general procedure C with 3,3,4,4-tetrafluoropyrrolidine hydrochloride. 26 was isolated in 86% yield as a white solid (0.813 mmol, 0.353 g). (R)-26 was isolated using preparative chiral HPLC separation (Lux® 5 μM Cellulose-1, LC Column, 250×21.2 mm, AXIA™ Packed, isocratic: 10% i-PrOH/hexanes). $^{1}$H NMR ($CD_3OD$, 500 MHz) δ: 7.60 (d, J=7.6 Hz, 1H), 7.54 (d, J=8.1 Hz, 1H), 7.38 (d, J=8.7 Hz, 2H), 7.22 (t, J=7.8 Hz, 1H), 6.82 (d, J=8.8 Hz, 2H), 3.45-3.24 (m, 2H, overlap with $CD_3OD$), 3.12 (q, J=12.5 Hz, 2H). $^{13}$C NMR ($CD_3OD$, 126 MHz) δ: 178.73, 159.27, 139.73 (q, J=2.1 Hz), 132.52, 130.19, 129.33, 128.43, 127.12 (q, J=4.5 Hz), 124.98 (q, J=271.0 Hz), 123.86, 119.90 (tt, J=260.5, 23.5 Hz), 116.87, 113.98 (q, J=33.4 Hz), 70.16, 54.26 (t, J=27.9 Hz). $^{19}$F NMR ($CD_3OD$, 471 MHz) δ: −63.72, −120.61 (t, J=13.2 Hz). HRMS (ESI): m/z calc. for $C_{19}H_{12}F_7N_2O_2[M-H]^-$ 433.0787, found: 433.0788. HPLC Chiral Purity (λ: 254 nm): >99%. Melting Point: 112.3-115.3° C.

(S)-26, (S)-3-(4-hydroxyphenyl)-3-(3,3,4,4-tetrafluoropyrrolidin-1-yl)-7-(trifluoromethyl) indolin-2-one, was isolated using preparative chiral HPLC separation (Lux® 5 μM Cellulose-1, LC Column, 250×21.2 mm, AXIA™ Packed, isocratic: 10% i-PrOH/hexanes). $^{1}$H NMR ($CD_3OD$, 500 MHz) δ: 7.60 (d, J=7.5 Hz, 1H), 7.54 (d, J=8.0 Hz, 1H), 7.38 (d, J=8.6 Hz, 2H), 7.22 (t, J=7.8 Hz, 1H), 6.82 (d, J=8.6 Hz, 2H), 3.58-3.25 (m, 2H, overlap with $CD_3OD$), 3.12 (q, J=12.5 Hz, 2H). $^{13}$C NMR ($CD_3OD$, 126 MHz) δ: 178.73, 159.28, 139.74 (q, J=2.2 Hz), 132.52, 130.20, 129.33, 128.43, 127.13 (q, J=4.5 Hz), 124.98 (q, J=271.0 Hz), 123.87, 119.91 (tt, J=260.5, 23.6 Hz), 116.87, 113.98 (q, J=33.3 Hz), 70.16, 54.26 (t, J=27.9 Hz). $^{19}$F NMR ($CD_3OD$, 471 MHz) δ: −63.73, −120.62 (t, 13.2 Hz). HRMS (ESI): m/z calc. for $C_{19}H_{12}F_7N_2O_2[M-H]^-$ 433.0787, found: 433.0786. HPLC Chiral Purity (λ: 254 nm): >99%. Melting Point: 99.0-101.6° C.

27, 3,3-bis(4-hydroxyphenyl)-7-(trifluoromethyl)indolin-2-one. A round bottom flask was charged with compound 2 (0.243 mmol, 0.10 g) and phenol (0.85 mmol, 0.080 g) were dissolved in dichloromethane (0.5 mL). The reaction mixture was then placed in an ice bath and triflic acid (TfOH, 0.09 mL) was then added dropwise. Caution: Triflic acid dissolves many common plastics, especially plungers of syringes, so using metal needles or glass syringes are recommended. If using a plastic syringe, avoid contact with the plunger of the syringe. The reaction stirred for 6 hours while the ice was allowed to melt. The reaction mixture was then poured into ice-filled saturated sodium bicarbonate (aqueous, ~10 mL) and the aqueous solution was extracted with ethyl acetate (3×). The combined organic layers were dried over sodium sulfate, filtered, and concentrated in vacuo. The resultant oil was then purified via column chromatography ($SiO_2$, Eluting solvent: an initial mixture 0:100 Ethyl Acetate:Hexanes with increasing gradient to 35:65 Ethyl Acetate:Hexanes (15 column volumes) followed by increasing to 70:30 Ethyl Acetate:Hexanes (7 column volumes) then 100:0 Ethyl Acetate:Hexanes (2 column volumes). 27 was isolated as a white solid (0.0480 mmol, 0.0185 g) and 2 as a white solid (0.0876 mmol, 0.0361 g). $^{1}$H NMR ($CD_3OD$, 500 MHz) δ: 7.49 (d, J=8.1 Hz, 1H), 7.39 (d, J=7.6 Hz, 1H), 7.17 (t, J=7.9 Hz, 1H), 7.01 (d, J=8.6 Hz, 4H), 6.72 (d, J=8.7 Hz, 4H). $^{13}$C NMR ($CD_3OD$, 126 MHz) δ: 182.44, 158.04, 139.71 (q, J=2.1 Hz), 138.04, 133.45, 130.98, 130.51, 125.65 (q, J=4.6 Hz), 125.24 (q, J=271.2 Hz), 123.30, 116.24, 113.51 (q, J=33.2 Hz), 62.14. $^{19}$F NMR ($CD_3OD$, 471 MHz) δ: −63.65. HRMS (ESI): m/z calc. for $C_{21}H_{18}F_3NO_3$ $[M+H]^+$ 386.1004, found: 386.1007.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as ‘Compound X’). A specific example of Compound X is ErSO-DFP.

| (i) Tablet 1 | mg/tablet |
|---|---|
| ‘Compound X’ | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| ‘Compound X’ | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| ‘Compound X’ | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/ml |
|---|---|
| ‘Compound X’ (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| ‘Compound X’ (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

(I)

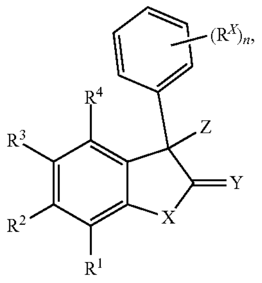

wherein

X is O, S, or $NR^A$,

Y is $NR^A$, O, or S;

each $R^A$ is independently H or alkyl;

$R^1$ is alkyl, cycloalkyl, halo, $—OR^B$, $—SR^B$, or $—N(R^B)_2$, wherein alkyl and cycloalkyl of $R^1$ is optionally substituted with one or more substituents;

$R^2$, $R^3$ and $R^4$ are each independently H, trifluoromethyl, alkyl, cycloalkyl, heterocycle, aryl, heteroaryl, halo, $—OR^B$, $—SR^B$, or $—N(R^B)_2$;

each $R^B$ is independently H, trifluoromethyl, or alkyl;

each $R^X$ is independently OH, halo, alkyl, $—OR^C$, $—SR^C$, $—S(=O)_2R^C$;

each $R^C$ is independently H, trifluoromethyl, or alkyl;

n is 1, 2, 3, 4, 5, or 0; and

Z is a 6-, 5-, 4-, 7-, or 8-membered nitrogen-containing heterocycle, wherein a nitrogen atom of the nitrogen-containing heterocycle is bonded to the benzylic carbon atom of Formula I and is substituted with one or more substituents;

or a salt thereof.

2. The compound of claim 1 wherein X is NH and Y is O.

3. The compound of claim 1 wherein $R^1$ is $CF_3$ or $CH_3$.

4. The compound of claim 1 wherein $R^2$, $R^3$ and $R^4$ are each independently H or halo.

5. The compound of claim 1 wherein $R^X$ is OH.

6. The compound of claim 1 wherein one $R^X$ group is bonded at the para- or meta-position of the phenyl ring.

7. The compound of claim 1 wherein n is 1, 2, or 3.

8. The compound of claim 1 wherein Z is a 6-membered nitrogen-containing heterocycle bonded at a nitrogen atom of the 6-membered nitrogen-containing heterocycle.

9. The compound of claim 8 wherein Z is substituted by two or one halo groups.

10. The compound of claim 1 wherein the Z is 4,4-difluoropiperidinyl.

11. The compound of claim 1 wherein the nitrogen-containing heterocycle is piperidine, pyrrolidine, morpholine, piperazine, azepane, each optionally substituted with one to six substituents.

12. The compound of claim 1 represented by Formula II or III:

(II)

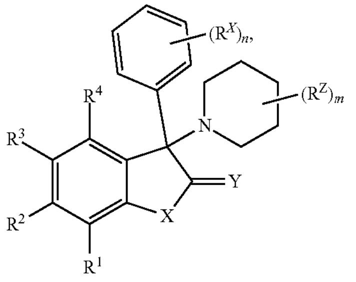

or (III)

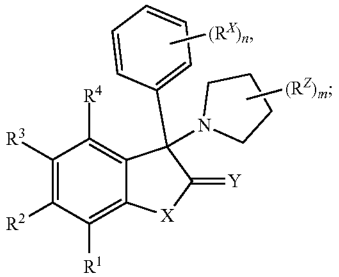

wherein each $R^Z$ is independently halo, nitro, alkyl, —$OR^D$, —$SR^D$, —$S(=O)_2R^D$; wherein each $R^D$ is independently H, trifluoromethyl, or alkyl; and m is 2, 0, 1, 3, 4, 5, 6, 7, or 8.

13. The compound of claim 12 wherein X is NH; Y is O; $R^1$ is $CF_3$ or $CH_3$; $R^2$, $R^3$ and $R^4$ are each independently H or halo; $R^X$ is OH, and n is 1, 2, or 3.

14. The compound of claim 12 wherein m is 2 and each $R^Z$ is halo.

15. The compound of claim 14 wherein each halo is fluoro.

16. The compound of claim 1 wherein the compound is 2, 24, or 26:

(2)

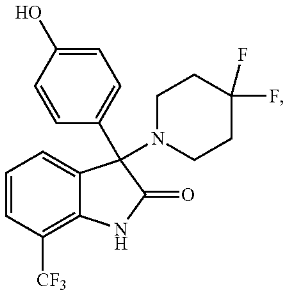

(24)

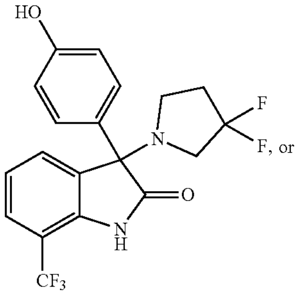

(26)

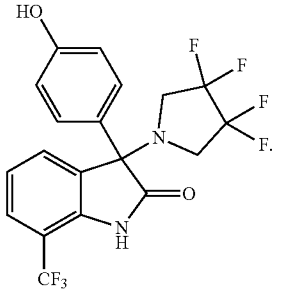

17. The compound ErSO-DFP ((R)-2):

(ErSO-DFP)

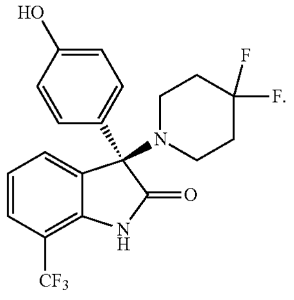

18. The compound of claim 1 wherein the compound is compound 26:

(26)

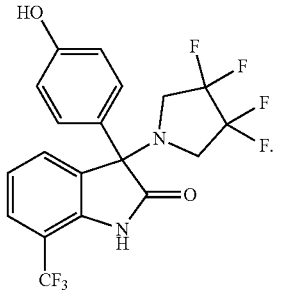

19. A pharmaceutical composition comprising the compound of claim 1 in combination with a pharmaceutically acceptable carrier.

20. A method of treating an ERα positive cancer comprising administering to subject having an ERα positive cancer a therapeutically effective amount of a compound of claim 1, wherein the ERα positive cancer is thereby treated.

21. The method of claim 20 wherein the ERα positive cancer is breast cancer, ovarian cancer, uterine cancer, cervical carcinoma, or endometrial cancer.

22. The method of claim 20 wherein the compound is:

(R)-3-(4,4-difluoropiperidin-1-yl)-3-(4-hydroxyphenyl)-7-(trifluoromethyl) indolin-2-one; or (S)-3-(4,4-difluoropiperidin-1-yl)-3-(4-hydroxyphenyl)-7-(trifluoromethyl) indolin-2-one; or (R)-3-(4-hydroxyphenyl)-3-(3,3,4,4-tetrafluoropyrrolidin-1-yl)-7-(trifluoromethyl) indolin-2-one; or (S)-3-(4-hydroxyphenyl)-3-(3,3,4,4-tetrafluoropyrrolidin-1-yl)-7-(trifluoromethyl) indolin-2-one.

* * * * *